US010400274B2

(12) United States Patent
Huie et al.

(10) Patent No.: US 10,400,274 B2
(45) Date of Patent: Sep. 3, 2019

(54) FLUOROGENIC PROBES AND THEIR USE IN QUANTITATIVE DETECTION OF TARGET RNA SEQUENCES

(71) Applicant: JAN BIOTECH, INC., Ithaca, NY (US)

(72) Inventors: Janet Lockwood Huie, Ithaca, NY (US); Jennifer Anastasia Nichols, Ithaca, NY (US); Deborah Allen Kuzmanovic, Ithaca, NY (US)

(73) Assignee: Jan Biotech, Inc., Ithaca, NY (US)

( * ) Notice: Subject to any disclaimer, the term of this patent is extended or adjusted under 35 U.S.C. 154(b) by 18 days.

(21) Appl. No.: 15/625,537

(22) Filed: Jun. 16, 2017

(65) Prior Publication Data

US 2018/0002743 A1    Jan. 4, 2018

Related U.S. Application Data

(60) Provisional application No. 62/351,918, filed on Jun. 18, 2016.

(51) Int. Cl.

| | | |
|---|---|---|
| *C12P 19/34* | (2006.01) | |
| *C12Q 1/6837* | (2018.01) | |
| *A61K 31/404* | (2006.01) | |
| *A61K 31/7115* | (2006.01) | |
| *C12Q 1/6818* | (2018.01) | |
| *C12Q 1/70* | (2006.01) | |
| *A61K 31/713* | (2006.01) | |

(52) U.S. Cl.
CPC .......... *C12Q 1/6837* (2013.01); *A61K 31/404* (2013.01); *A61K 31/713* (2013.01); *A61K 31/7115* (2013.01); *C12Q 1/6818* (2013.01); *C12Q 1/702* (2013.01); *C12Q 1/703* (2013.01); *C12N 2740/16052* (2013.01); *G01N 2333/16* (2013.01); *Y02A 50/391* (2018.01); *Y02A 50/465* (2018.01)

(58) Field of Classification Search
CPC ............ C12Q 1/6818; C12Q 2565/101; C12Q 1/6837; C12Q 1/702; C12Q 1/703; A61K 31/404; A61K 31/7115; C12N 2740/16052; G01N 2333/16; Y02A 50/391
USPC ....................................................... 435/91.2
See application file for complete search history.

(56) References Cited

U.S. PATENT DOCUMENTS

| 2012/0115136 | A1 | 5/2012 | Buchardt et al. | |
| 2015/0017650 | A1* | 1/2015 | Mancebo ............. | C12Q 1/6862 435/6.12 |

OTHER PUBLICATIONS

Meguellati et al. (2013) J. Analyt. Molecul Tech 1 (1):5.*
Madruga et al. (2007) Lancet 370:29-38.*
Koripelly et al. (2010) Bioconjugate chem vol. 21: 2103-2109.*
Abe et al., PNAS, vol. 103, No. 2, pp. 263-268, Jan. 2006.*
Rodriquez-Inigo et al., "Detection of Human Immunodeficiency Virus Type 1 RNA by In Situ Hybridization in Oral Mucosa Epithelial Cells From Anti-HIV-1 Positive Patients", Journal of Medical Virology, vol. 77, No. 17, 20015, 6 pages.
Roloff et al., "The role of reactivity in DNA templated native chemical PNA ligation during PCR", Bioorganic & Medicinal Chemistry 21; 2013, 7 pages, Germany.
Shafi et al., "Androgen receptors in hormone-dependent and castration-resistant prostate cancer", Pharmacology & Therapeutics 140, 2013, 16 pages.
Shan et al., "From reactivation of latent HIV-1 to elimination of the latent reservoir: The presence of multiple barriers to viral eradication", Bioessays Journal 35, 2013, 9 pages.
Shibata et al., Oligonucleotide-Templated Reactions for Sensing Nucleic Acids:, www.mdpi.com/journal/molecules, Molecutes ISSN 1420-3049, Feb. 2012, 18 pages.
Shiraki-Iida et al., "Structure of the mouse klotho gene and its two transcripts encoding membrane and secreted protein", FEBS Letters 424; 1998, 5 pages.
Siegel et al., "Cancer Statistics, 2014", CA Cancer J. Clin, vol. 64, No. 1 Jan./Feb. 2014, 21 pages.
Silverman et al., "Quenched Autoligation Probes", Methods in Molecular Biology, vol. 429: Molecular Beacons: Signallying Nucleic Acid Probes, Methods and Protocols, 2008, 10 pages.
Strain et al. "Highly Precise Measurement of HIV DNA by Droplet Digital PCR", PLOS One vol. 8, Issue 4, Apr. 2013, 8 pages.
Strain et al., "New Assays for monitoring residual HIV burden in effectively treated individuals", NIH Public Access, Curr Opin HIV AIDS, Mar. 2013, 9 pages.
Sun et al., "Castration resistance in human prostate cancer is conferred by a frequently occurring androgen receptor splice variant", The Journal of Clinical Investigation, vol. 120, No. 8, Aug. 2010, 16 pages.
Sun et al., "Template-Directed Fluorogenic Olignucleotide Ligation Using "Click" Chemistry: Detection of Single Nucleotide Polymorphism in the Human p53 Tumor Suppressor Gene", Bioconjugate Chemistry, 2013 American Chemical Society, 9 pages.
Tamura et al., "Detection of pre-mRNA splicing in vitro by an RNA-templated fluorogenic reaction", Bioorganic & Medical Chemistry Letters 22, Jun. 2012, 4 pages.
Tang et al., "Characterization of the Regulation of CD46 RNA Alternative Splicing", The Journal of Biological Chemistry, vol. 291, No. 27, 14 pages.

(Continued)

*Primary Examiner* — Cynthia B Wilder
(74) *Attorney, Agent, or Firm* — McNeill Baur PLLC

(57) ABSTRACT

Disclosed are compositions, reagents, methods, assays, and kits for quantitative and sensitive detection of target ribonucleic acid (RNA) sequences, particularly target RNA sequences that contain RNA spliced sites, hairpin stem-loops or other topological configurations of RNA secondary, tertiary, and quaternary structure, as well as linear RNA sequences. In some embodiments, fluorogenic modified-backbone oligonucleotide probes are employed for specific sequence hybridization across the target site, followed by chemical autoligation to produce a fluorescent molecule within the ligated probes. The autoligation detection reaction is performed isothermally or through thermocycling.

13 Claims, 13 Drawing Sheets

Specification includes a Sequence Listing.

(56) References Cited

OTHER PUBLICATIONS

Tee et al., "Alternative splicing of DENND1A, a PCOS candidate gene, generates variant 2", Molecular and Cellular Endocrinology, Jun. 5, 2016.
Thadani-Mulero et al., "Androgen Receptor Splice Variants Determine Taxane Sensitivity in Prostate Cancer", NIH Public Access, Cancer Res. Apr. 15, 2014, 22 pages.
Vacharaksa et al., "Oral Keratinocytes support non-replicative infection and transfer of harbored HIV-1 to permissive cells", Retrovirology, Bio Med Central, Jul. 17, 2008, 14 pages.
Wang et al., "The BRCA1-11q Alternative Splice Isoform Bypasses Germ;line Mutations and Promotes Therapeutic Resistance to PARP Inhibition and Cisplatin", Therapeutics, Targets, and Chemical Biology—American Association for Cancer Research, Jun. 1, 2016, 15 pages.
Yohannes et al., "Proteomic Signatures of Human Oral Epithelial Cells in HIV-Infected Subjects", PLoS One, vol. 6, Issue 11, Nov. 2011, 14 pages.
Yu et al. "Rapid Indcution of Androgen Receptor Splice Variants by Androgen Deprivation in Prostate Cancer", NIH public access, Clin Cancer Res., Mar. 15, 2014, 21 pages.
Zhang et al., "CD82 suppresses CD44 alternative splicing-dependent melanoma metastasis by mediating U2AF2 ubiquitination and degration", HHS Public Access Oncogene, Sep. 22, 2016, 30 pages.
Abe et al., "Flow Cytometric Detection of Specific RNAs in native human cells with quenched autoligating FRET probes", PNAS, vol. 103, No. 2, Jan. 10, 2016; 6 pages.
Abe et al., "Rapid DNA Chemical Ligation for Amplification of RNA and DNA Signal", Bioconjugate Chemistry vol. 19, Nov. 9, 2007, 7 pages.
Antonarakis et al. "AR-V7 and Resistance to Enzalutamide and Abiraterone in Prostate Cancer", The New England Journal of Medicine, downloaded from nejm.org on Apr. 11, 2017, 11 pages.
Bruner et al., "Towards an HIV-1 cure: measuring the latent reservoir", HHS Public Access, Trends Microbiol, Apr. 2015, 24 pages.
Cao et al. "20(S)-Protopanaxadiol-aglycone Downregulation of the full-length and Splice Variants of Androgen Receptor", NIH Public Access, Int. J. Cancer, Mar. 15, 2013, 20 pages.
Cetin et al., "Prevalence of Patients with Nonmetastatic Prostate Cancer on Androgen Deprivation Therapy in the United States", Health Outcomes Research, 2013, 6 pages.
Chun et al. "HIV reservoirs: pathogenesis and obstacles to viral eradication and cure", Wolters Kluwer Health, Lippincott Williams & Wilkins, 2012, 8 pages.
Chun et al., "Re-Emergence of HIV after stopping therapy", Macmillan Magazines LTD, Nature, vol. 401, Oct. 29, 1999, 2 pages.
Deere et al., "Analysis of Multiply Spliced Transcripts in Lymphoid Tissue Reservoirs of Rhesus Macaques Infected with RT-SHIV during HAART", PLOS One, vol. 9, Issue 2, Feb. 2014, 10 pages.
Dolatshad et al., "Cryptic splicing events in the iron transporter ABCB7 and other key target genes in SF3B1-mutant myelodysplastic syndromes", Leukemia, 2016, 10 pages.
Efstathiou et al., "Molecular Characterization of Enzalutamide-treated Bone Metastatic Castration-resistant Prostate Cancer", European Urology—Science Direct, 2014, 8 pages.
Eriksson et al., "Comparative Analysis of Measures of Viral Reservoirs in HIV-1 Eradication Studies", PLOS Pathogens, vol. 9, Issue 2, Feb. 2013, 17 pages.
Ferraldeschi et al., "Second-generation HSP90 inhibitor onalespib blocks mRNA splicing of androgen receptor variant 7 in prostate cancer cells", HHS Public Access, Cancer Res. May 1, 2016, 23 pages.
Franzini et al., "Two Successive Reactions on a DNA Template: A Strategy for Improving Background Fluorescence and Specificity in Nucleic Acid Detection", Chemistry : A European Journal, 2011, 8 pages.
Franzini et al., "Two Successive Reactions on a DNA Template: A Strategy for Improving Background Fluorescence and Specificity in Nucleic Acid Detection" Supporting Information, Chemistry : A European Journal, 2011, 10 pages.
Gorska et al., "Reactions Templated by Nucleic Acids: More Ways to Translate Oligonucleotide-Based Instructions into Emerging Function", Angewandte Reviews International Edition, 2013, 24 pages.
Gowda et al., "Inhibition of Hedgehog and Androgen receptor signalling pathways produced synergistic suppression of castration-resistant prostate cancer progression", NIH Public Access, Mol Cancer Res. Nov. 2013, 21 pages.
Guo et al., "A New Trick of an Old Molecule: Androgen Receptor Splice Variants Taking the Stage?!", International Journal of Biological Sciences, vol. 7, Jul. 6, 2011, 8 pages.
Harcourt et al., "Amplified microRNA detection by templated chemistry", Published online Nucleic Acids Research, vol. 40, No. 9, 2012, 8 pages.
Harrigan et al., "Rate of HIV-1 RNA rebound upon stopping antiretroviral therapy", AIDS, 1999, 4 pages.
Hermankova et al., "Analysis of Human Immunodeficiency Virus Type 1 Gene Expression in Latently Infected Resting CD4+ T Lymphocytes in Vivo", Journal of Virology, Jul. 2003, 10 pages.
Herzberg et al., "Plausibility of HIV-1 Infection of Oral Mucosal Epithelial Cells", International & American Associations for Dental Research, 2011, 7 pages.
Ho et al., "Replication-competent non-induced proviruses in the latent reservoir increase barrier to HIV-1 cure", NIH Public Access, Cell, Oct. 24, 2013, 21 pages.
Hong et al., "Identification of Alternative Splicing and Fusion Transcripts in in Non-Small Cell Lung Cancer by RNA Sequencing", The Korean Academy of Tuberculosis and Respiratory Diseases, 2016, 6 pages.
Hu et al., "Distinct transcriptional programs mediated by the ligand-depdendent full-length androgen receptor and its splice variants in castration-resistant prostate cancer", NIH Public Access, Cancer Res. Jul. 15, 2012, 11 pages.
Hu et al., "Ligand-independent Androgen Receptor Variants Derived from Splicing of Cryptic Exons Signify Hormone Refractory Prostate Cancer", NIH Public Access, Jan. 1, 2009, 13 pages.
Huang et al. "HIV-1 reactivation in HIV-latently infected dendritic cells by oral micoorganisms and LPS", Cellular Immunology 268, 2011, 7 pages.
Jacquenet et al., "Conserved stem-loop structures in the HIV-1 RNA region containing the A3 3' splice site and its cis-regulatory element: possible involvement in RNA splicing", Oxford University Press, Nucleic Acids Research, 2001, vol. 29, No. 2, 15 pages.
Koripelly et al., Dual Sensing of Hairpin and Quadruplex DNA Structures Using Multicolored Peptide Nucleic Acid Fluorescent Probes, Bioconjugate Chem, 2010, pp. 2103-2109, vol. 21, No. 11.
Kuzmanovic et al., "A novel application of small-angle scattering techniques: Quality assurance testing of virus quantification technology", ScienceDirect, Radiation Physics and Chemistry 77, 2008, 10 pages.
Kuzmanovic et al., "Bacteriophage MS2: Molecular Weight and Spatial Distribution of the Protein and RNA Components by Small-Angle Neutron Scattering and Virus Counting", Elsevier Science Ltd. vol. 11; 2003, 10 pages.
Laird et al., "Rapid Quantification of the Latent Reservoir for HIV-1 Using a Viral Outgrowth Assay", PLOS Pathogens, vol. 9, Issue 5, May 2013, 11 pages.
Lassen et al., "Analysis of Human Immunodeficiency Virus Type 1 Transcriptional Elongation in Resting CD4+ T Cells in Vivo", Journal of Virology, Sep. 2004, vol. 78, No. 17, 10 pages.
Lassen et al., "Nuclear Retention of Multiply Spliced HIV-1 RNA in Resting CD4+ T Cells", PLoS Pathogens, vol. 2, Issue 7, Jul. 2006; 12 pages.
Li et al. "Methods for Identifying and Quantifying mRNA Expression of Androgen Receptor Splicing Variants in Prostate Cancer", The Nuclear Receptor Superfamily: Methods and Protocols, Methods in Molecular Biology, vol. 1443, 2016, 13 pages.
Li et al., "Androgen receptor splice variants mediate enzalutamide resistance in castration-resistant prostate cancer cell lines", NIH Public Access, Cancer Res. Jan. 15, 2013, 11 pages.

(56) References Cited

OTHER PUBLICATIONS

Liu et al. "Complex Impacts of PI3K/AKT Inhibitors to Androgen Receptor Gene Expression in Prostate Cancer Cells", PLOS One, vol. 9, Issue 10, Oct. 2014, 9 pages.
Livak et al., "Oligonucleotides with Fluorescent Dyes at Opposite Ends Provide a Quenched Probe System Useful for Detecting PCR Product and Nucleic Acid Hybridization", Cold Spring Harbor Laboratory Press, 1995, 7 pages.
Lu et al. "The cistrome and gene signature of androgen receptor splice variants in castration-resistant prostate cancer cells", HHS Public Access, J. Urol. Feb. 2015, 19 pages.
Maguellati et al., DNA-Templated Synthesis of Trimethine Cyanine Dyes: A Versatile Fluorogenic Reaction for Sensing G-Quadruplex Formation, Angewandte Chemie, Wiley-VCH 2010, Supporting information; 17 pages; Germany.
Maguellati et al., DNA-Templated Synthesis of Trimethine Cyanine Dyes: A Versatile Fluorogenic Reaction for Sensing G-Quadruplex Formation, Wiley InterScience; 2010, 5 pages, Germany.
Mansfield, Elizabeth A. "FDA Perspective on Companion Diagnostics: An Evolving Paradigm"; American Association for Cancer Research; 2014, download Jul. 27, 2017; 6 pages.
Massanella et al. "Quantification of Total and 2-LTR (Long terminal repeat) HIV DNA, HIV RNA and Herpesvirus DNA in PBMCs", HHS Public Access, Bio Protoc, Jun. 5, 2015, 21 pages.
Massanella et al., "Measuring the latent reservoir in vivo", The Journal of Clinical Investigation, Feb. 22, 2016, 9 pages.
Meguellati et al., Single Nucleotide Polymorphism Detection Using a Biocompatiable, Fluorogenic and DNA-Templated Reaction of Cyanine Dye Formation, Avens Publishing Group, J Analyt Molecul Tech, Dec. 2013, 5 pages, vol. 1; Issue 1, France.
Nolan et al., "Quantification of mRNA using real-time RT-PCR", Nature Protocols, vol. 1, No. 3, 2006, 24 pages.
Nutter et al., "Dysregulation of RBFOX2 is an early event in cardiac pathogenesis of diabetes", HHS Public Access, Cell Rep. Jun. 7, 2016, 27 pages.
Ocwiega et al., "A Reverse Transcription Loop-Mediated Isothermal Amplification Assay Optimized to Detect Multiple HIV Subtypes", PLOS One, Feb. 12, 2015, 11 pages.
Peacock et al., "Vav3 Enhances Androgen Receptor Splice Variant Activity and Is Critical for Castration-Resistant Prostate Cancer Growth and Survival", The Endocrine Society, Sep. 28, 2012, 23 pages.
Purcell et al., "Alternative Splicing of Human Immunodeficiency Virus Type 1 mRNA Modulates Viral Protein Expression, Replication, and Infectivity", Journal of Virology, Nov. 1993, 14 pages.
AMPLICOR HIV-1 Monitor™ Test; Product Information; 53 pages, downloaded on Aug. 2, 2018 at www.fda.gov/downloads/BiologicsBloodVaccines/BloodBloodProducts/ApprovedProducts/PremarketApprovalsPMAs/ucm093317.pdf.

* cited by examiner

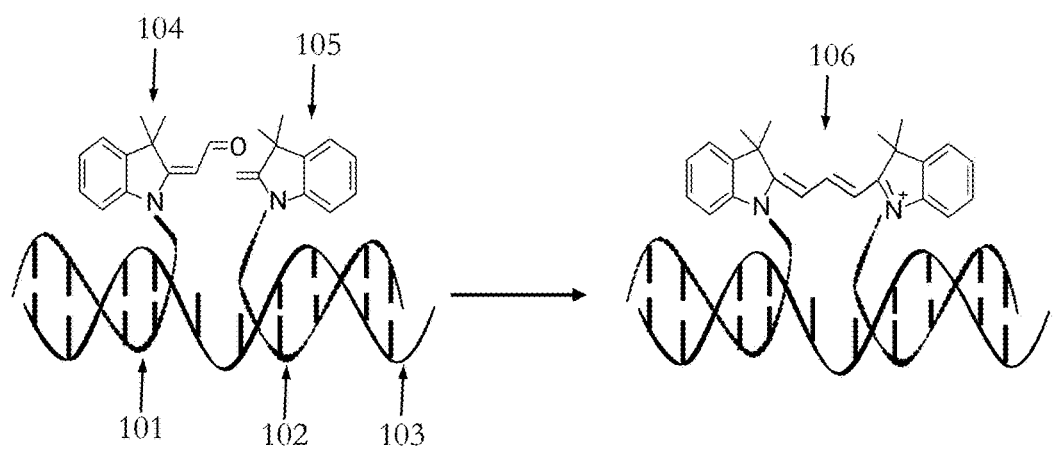
Fig. 2a
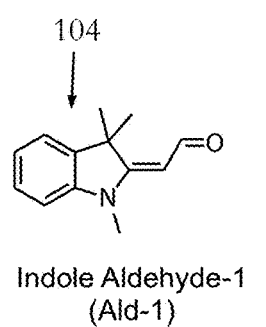
Indole Aldehyde-1
(Ald-1)
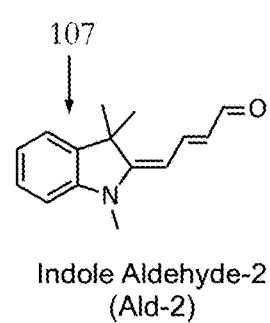
Indole Aldehyde-2
(Ald-2)
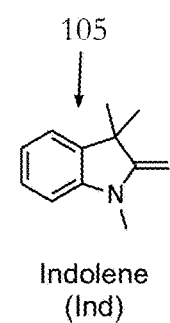
Indolene
(Ind)
Fig. 2b     Fig. 2c     Fig. 2d

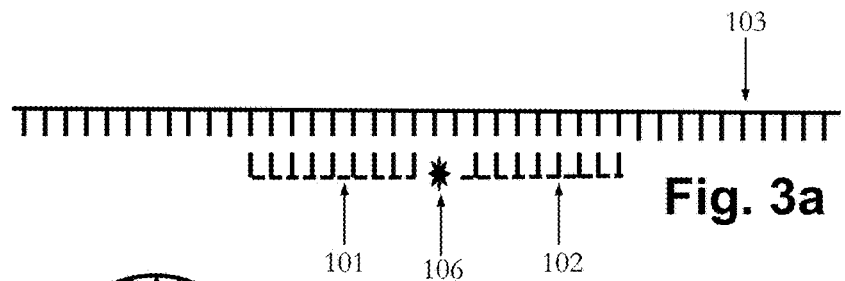
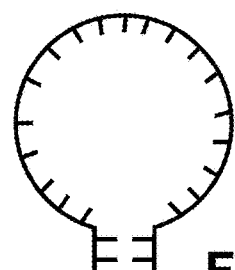
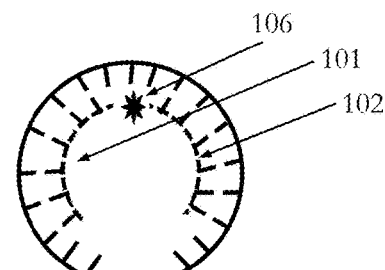
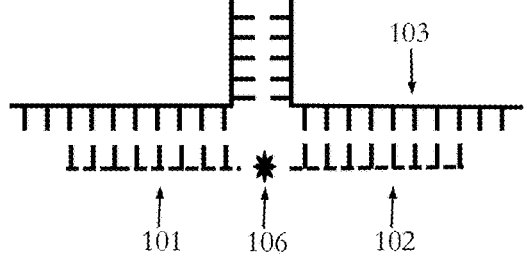
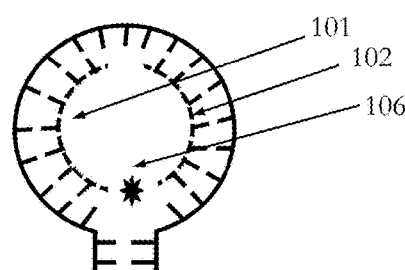
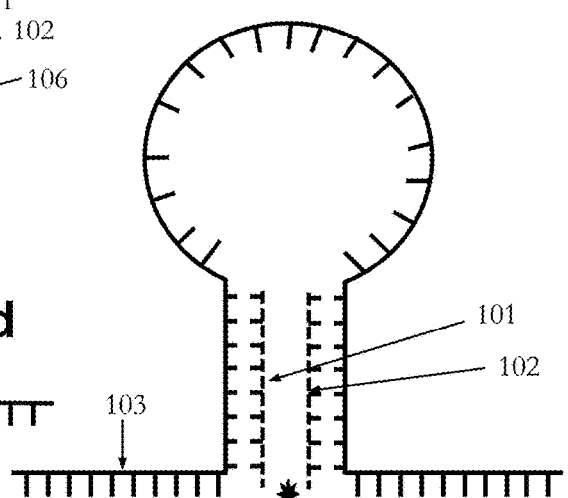

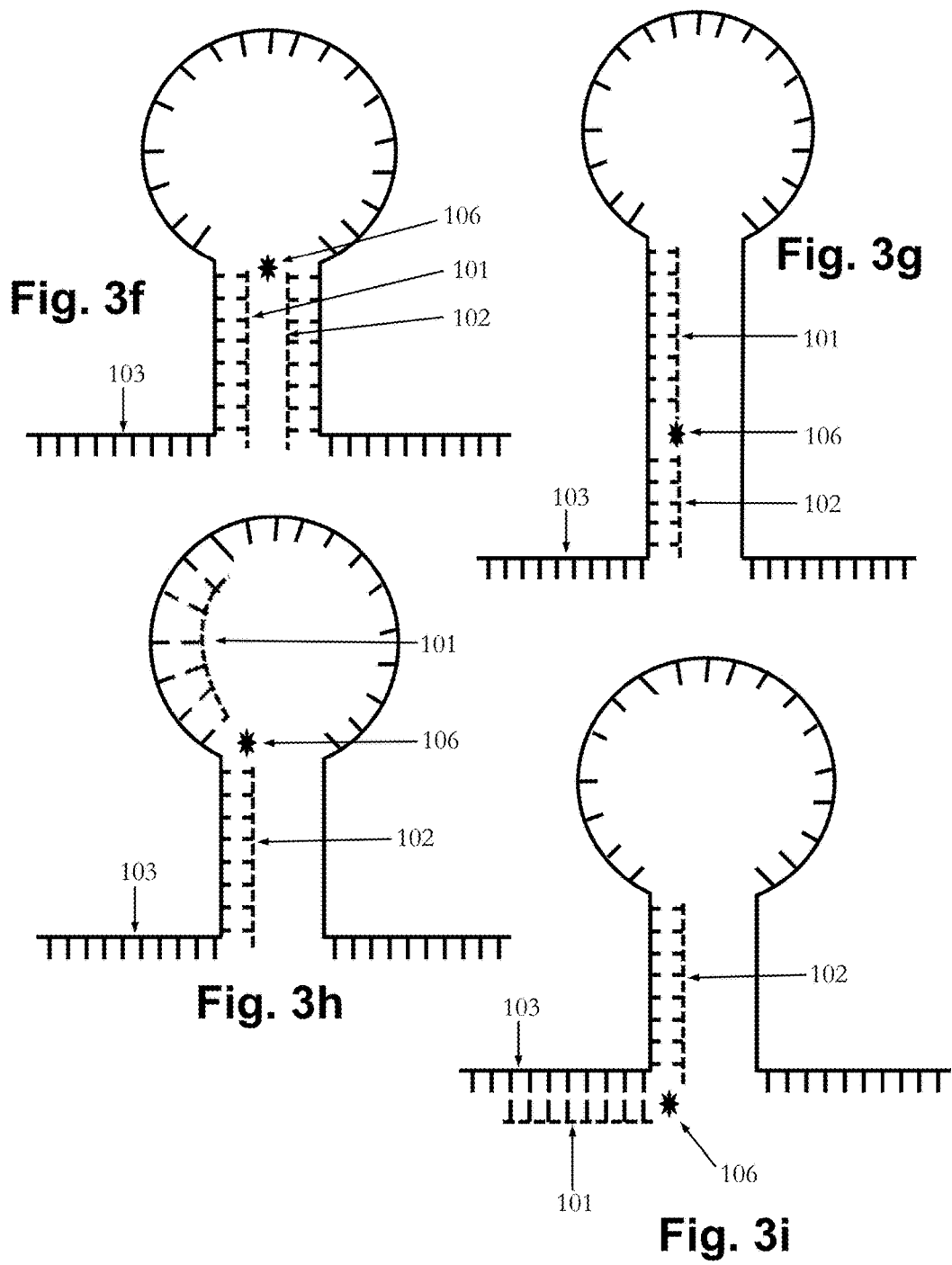

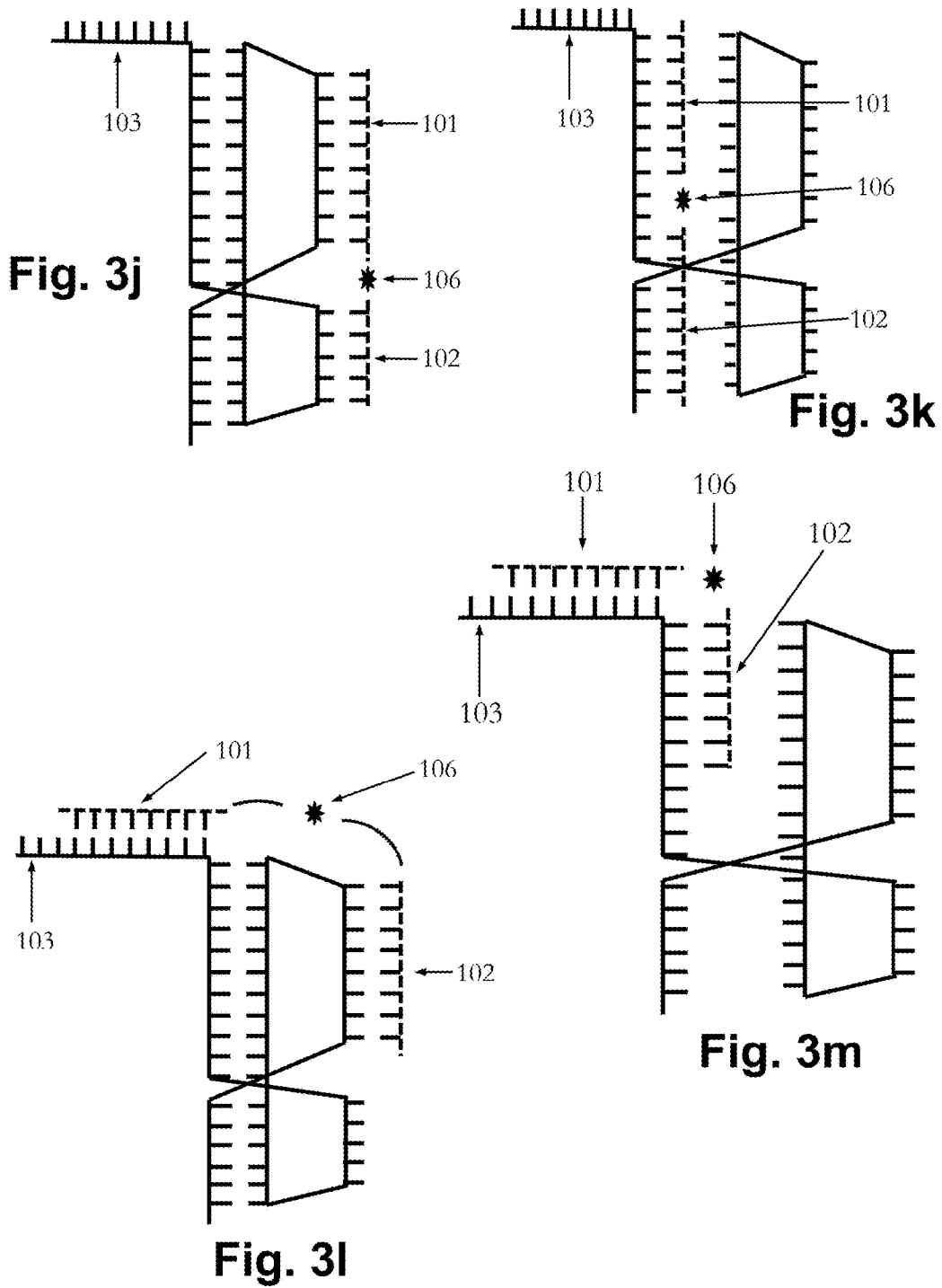

```
                          SEQUENCE LISTING

<160> NUMBER OF SEQ ID NOS: 16

<210> SEQ ID NO 1
<211> LENGTH: 17
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(1)
<223> OTHER INFORMATION: Fluorogenic probe moiety attachment position on
      probe sequence

<400> SEQUENCE: 1
cctgtatcta atagagc                                                    17

<210> SEQ ID NO 2
<211> LENGTH: 18
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (18)..(18)
<223> OTHER INFORMATION: Fluorogenic probe moiety attachment position on
      probe sequence

<400> SEQUENCE: 2
tctaatactg tatcatct                                                   18

<210> SEQ ID NO 3
<211> LENGTH: 16
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(1)
<223> OTHER INFORMATION: Fluorogenic probe moiety attachment position on
      probe sequence

<400> SEQUENCE: 3
ttgtactgtg ctgaca                                                     16

<210> SEQ ID NO 4
<211> LENGTH: 16
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (16)..(16)
<223> OTHER INFORMATION: Fluorogenic probe moiety attachment position on
      probe sequence

<400> SEQUENCE: 4
gcctaattcc atgtgt                                                     16

<210> SEQ ID NO 5
<211> LENGTH: 15
```

```
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(1)
<223> OTHER INFORMATION: Fluorogenic probe moiety attachment position on
      probe sequence

<400> SEQUENCE: 5
atagtgcttc ctgct                                                      15

<210> SEQ ID NO 6
<211> LENGTH: 15
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (15)..(15)
<223> OTHER INFORMATION: Fluorogenic probe moiety attachment position on
      probe sequence

<400> SEQUENCE: 6
gtcattgagg ctgcg                                                      15

<210> SEQ ID NO 7
<211> LENGTH: 16
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(1)
<223> OTHER INFORMATION: Fluorogenic probe moiety attachment position on
      probe sequence

<400> SEQUENCE: 7
gaagaggcac aggctc                                                     16

<210> SEQ ID NO 8
<211> LENGTH: 15
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (15)..(15)
<223> OTHER INFORMATION: Fluorogenic probe moiety attachment position on
      probe sequence

<400> SEQUENCE: 8
tctcaagcgg tggta                                                      15

<210> SEQ ID NO 9
<211> LENGTH: 5
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(1)
<223> OTHER INFORMATION: Fluorogenic probe moiety attachment position on
      probe sequence
<220> FEATURE:
<221> NAME/KEY: misc_feature
```

```
<222> LOCATION: (1)..(5)
<223> OTHER INFORMATION: Peptide nucleic acid: 5' Ald-CTTTG-DMLys-DMLys-
      CONH2

<400> SEQUENCE: 9 ctttg                                                                        5

<210> SEQ ID NO 10
<211> LENGTH: 5
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(5)
<223> OTHER INFORMATION: Peptide nucleic acid: 3' Ind-TGGGT-DMLys-DMLys-
      CONH2
<220> FEATURE:
<221> NAME/KEY: misc_feature
<222> LOCATION: (5)..(5)
<223> OTHER INFORMATION: Fluorogenic probe moiety attachment position on
      probe sequence

<400> SEQUENCE: 10 tgggt                                                                        5

<210> SEQ ID NO 11
<211> LENGTH: 15
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(1)
<223> OTHER INFORMATION: Fluorogenic probe moiety attachment position on
      probe sequence

<400> SEQUENCE: 11
ctytgrtaba rrady                                                            15

<210> SEQ ID NO 12
<211> LENGTH: 15
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(2)
<223> OTHER INFORMATION: n is a, c, g, or t
<220> FEATURE:
<221> NAME/KEY: misc_feature
<222> LOCATION: (4)..(4)
<223> OTHER INFORMATION: n is a, c, g, or t
<220> FEATURE:
<221> NAME/KEY: misc_feature
<222> LOCATION: (11)..(11)
<223> OTHER INFORMATION: n is a, c, g, or t
<220> FEATURE:
<221> NAME/KEY: misc_feature
<222> LOCATION: (15)..(15)
<223> OTHER INFORMATION: Fluorogenic probe moiety attachment position on
      probe sequence

<400> SEQUENCE: 12
nnbnkggrdr nggrt                                                            15

<210> SEQ ID NO 13
<211> LENGTH: 11
```

```
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(1)
<223> OTHER INFORMATION: Fluorogenic probe moiety attachment position on
      probe sequence

<400> SEQUENCE: 13
ctctgggctt g                                                           11

<210> SEQ ID NO 14
<211> LENGTH: 12
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (12)..(12)
<223> OTHER INFORMATION: Fluorogenic probe moiety attachment position on
      probe sequence

<400> SEQUENCE: 14
gaaatggcag gg                                                          12

<210> SEQ ID NO 15
<211> LENGTH: 12
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (1)..(1)
<223> OTHER INFORMATION: Fluorogenic probe moiety attachment position on
      probe sequence

<400> SEQUENCE: 15
ccagttgcag ca                                                          12

<210> SEQ ID NO 16
<211> LENGTH: 12
<212> TYPE: DNA
<213> ORGANISM: Artificial Sequence
<220> FEATURE:
<223> OTHER INFORMATION: Latent HIV-1 qLDR Oligonucleotide Probe
<220> FEATURE:
<221> NAME/KEY: misc_feature
<222> LOCATION: (12)..(12)
<223> OTHER INFORMATION: Fluorogenic probe moiety attachment position on
      probe sequence

<400> SEQUENCE: 16
ctgggaggag cg                                                          12
```

FLUOROGENIC PROBES AND THEIR USE IN QUANTITATIVE DETECTION OF TARGET RNA SEQUENCES

This application claims priority to U.S. Provisional Application No. 62/351,918, filed on Jun. 18, 2016, which is hereby incorporated by reference in its entirety.

This invention was made with government support under STTR Phase I Award #1R41AI116358-01A1and SBIR Phase I Award #1R43DE025437-01, awarded by the National Institutes of Health. The government has certain rights in the invention.

FIELD

Novel compositions, reagents, methods, assays, and kits within the field of fluorogenic, nonenzymatic, quantitative autoligation detection reactions, and their use in research, diagnostic, and clinical applications to rapidly, precisely, and accurately quantitate low levels of target ribonucleic acid (RNA) sequences present in a test sample.

BACKGROUND

With the introduction of combination/highly active antiretroviral therapy (cART or HAART) in 1996, the diagnosis of HIV/AIDS is no longer a death sentence. However, due to the existence of latent pools of HIV infected cells ("latent reservoirs," or "LR") in patients on HAART, HIV viral levels rapidly rebound upon cessation of treatment. Thus, HIV infected individuals must commit to lifelong adherence to HAART regimens, with an estimated cost of over half a million dollars per individual. Significant government and industry resources have been deployed to generate a cure for HIV/AIDS. Formed in 1986, the National Institutes of Health, Division of AIDS (DAIDS) was tasked with a national research agenda to end the HIV/AIDS epidemic. DAIDS supports a global research portfolio on HIV/AIDS, related co-infections, and co-morbidities. The goal is to create an AIDS-free Generation, through innovative approaches aimed at: 1) halting the spread of HIV through effective and acceptable prevention strategies and a preventive vaccine; 2) treating and curing HIV infection; 3) establishing treatment and prevention strategies for the HIV co-infections and co-morbidities of greatest significance; and 4) partnering with scientific and community stakeholders to implement effective interventions." If a cure becomes available, it will transform the lives of HIV-infected individuals and the financial landscape of this devastating disease. The ability to precisely and accurately measure low levels of HIV in latent reservoirs is a critical bottleneck in achieving a cure for HIV/AIDS.

Latent reservoirs consist of resting or memory CD4+ cells and other cells carrying, for example, the HIV-1 viral genome, either as pre-integration plasmids or integrated into relatively inactive regions of the DNA of CD4+ and potentially other host cells, as well as HIV-infected cells in HAART-inaccessible regions of the body. HIV-1 latent reservoirs include peripheral blood, lymph nodes (B cell follicles), gut-associated lymphatic tissue (GALT), central nervous system (brain and spinal cord), and oral mucosa.

Resting memory CD4+ T cells, typically sampled from peripheral blood mononuclear cells (PBMC), are a major component of the HIV-1 latent reservoir and stand as a major barrier to curing HIV-1 infection. While a variety of PCR- and culture-based assays have been developed to measure the size of the peripheral blood LR, there is little agreement between different assay results and no available assay appears to provide an accurate measurement of reservoir size. The lack of an accepted standard assay has remained a significant impediment in clinical trials seeking to evaluate novel HIV-1 eradication strategies. Well-validated, high-throughput assays that accurately quantitate latent reservoirs are urgently needed to assess complete eradication of HIV. Currently, there are no commercially or noncommercially available assays that adequately answer this need and which can be translated to widespread use.

The oral mucosa is a HAART-resistant HIV-1 latent reservoir (LR), which, unlike systemic immunity, is not restored to full immune competence by HAART treatment. The oral mucosa LR appears to include not only the expected CD4+ T cells, but also dendritic cells under constant reactivation by oral microbes and endotoxin. Further, oral epithelial cells, such as keratinocytes, may be susceptible to HIV infection and contribute to the oral HIV LR. The oral cavity is highly accessible for sequential noninvasive sampling and can routinely be sampled in outpatient or remote areas where resources are limited. A point-of-care assay that accurately and precisely quantifies the HIV-1 LR, along with corresponding viral output, from oral mucosa test samples would greatly facilitate development and dispensation of a cure for HIV AIDS.

The challenges in developing a quantitative diagnostic for the HIV latent reservoir are several: (1) low levels of HIV RNAs produced by latently infected cells; (2) variable expression of HIV RNAs produced by latently infected cells; (3) low levels of latently infected cells; and (4) the lack of reliable sampling methods for measuring HIV RNA levels from anatomical locations most relevant to eradicating the latent reservoir.

The quantitative ligation detection reaction (qLDR) technology provides a significantly improved molecular assay to accurately and precisely quantitate target RNA sequences and target RNA-producing cells, such as those present in latent HIV reservoirs. In an exemplary embodiment applying qLDR technology, latent HIV-1 RNA cells present in HIV-1 infected individuals on HAART are quantitated by accurately and precisely detecting spliced HIV mRNA directly from lysed CD4+-enriched peripheral mononuclear cells and oral mucosal cells.

qLDR employs a fluorogenic chemical autoligation reaction template by specific RNA sequences. In the closest prior art, a similar fluorogenic autoligation reaction provides detection of DNA G-quaduplexes and DNA single-nucleotide polymorphisms (Koripelly et al., 2010; Meguellati et al., 2010, 2013). However, fluorogenic autoligation detection reactions have not been developed for RNA spliced sites, RNA secondary structure, linear RNA sequences, nor for cell-based viral RNA. Autoligation detection reactions for RNA targets are in particular demand due a dearth of RNA-templated enzymatic reactions. While DNA-targeted fluorogenic autoligation detection has been used for limited testing of highly pure, artificial DNA constructs (Koripelly et al., 2010; Meguellati et al., 2010, 2013), RNA-targeted fluorogenic autoligation detection has not been developed and, after the present developments, has great promise for in vitro diagnostics. Beyond the difference in target (RNA vs. DNA), adaptation of autoligation reactions to RNA detection entails the formation of different probe-target structures which alter the chemistry of the reaction, different spacing between probes on the target sequence, the ability to detect significantly lower concentrations of target sequences in complex environments, the amount of variation in target tolerated by the probes, the ability to perform the reaction with and without denaturing and/or in isothermal or thermocycling conditions, the use of probe backbones that favor RNA binding, and the ability to use a much wider range of nonfluorescent reactive probe moieties to form a much wider range of fluorescent dyes for better detection and multiplex detection of multiple RNA targets.

In the past, direct detection of RNA has been difficult to achieve except by the use of hybridizing probes, which entail lengthy hybridization periods and multiple wash steps, followed by visualization procedures. There is a lack of RNA-specific enzymes similar to those used with DNA that achieve PCR amplification, single-nucleotide polymorphism (SNP) detection, and detection of specific RNA sequences and secondary structures. Thus, new methods for detecting RNA targets would benefit technology.

BRIEF SUMMARY

Disclosed are compositions, reagents, methods, assays, and kits for highly sensitive, precise and accurate detection of specific target ribonucleic acid (RNA) sequences, particularly RNA sequences containing spliced sites, as well as RNA sequences containing RNA stem-loops or other topological configurations generated through RNA secondary structure, but also including RNA sequences that do not contain such features. The compositions, reagents, methods, assays, and kits employ novel quantitative ligation detection reaction (qLDR) technology for direct quantitation of very low RNA levels in a test sample. In some embodiments, short, fluorogenic, modified-backbone probes are used for specific sequence hybridization across a target site, followed by chemical autoligation to produce a fluorescent molecule within the ligated probes. The autoligation detection reaction is performed isothermally or through thermocycling.

The novel compositions, reagents, methods, assays, and kits enable rapid, precise, and accurate quantitation of low levels of target RNA sequences present in a test sample. In an exemplary embodiment, pairs of fluorogenic, modified oligonucleotide probes are engineered to provide superior stability and highly-specific HIV-1 RNA detection for quantifying latent and activated HIV-1-infected reservoirs.

In experimental testing, probe pairs targeting HIV-1 sites conserved across HIV-1 types provided real-time, direct detection of HIV-1 RNAs, with highly precise and accurate quantification of the levels of HIV-1 mRNAs present, allowing detection of down to the level of one (1) latent HIV-1-infected cell in $10^6$ white blood cells from 20-30 mL of whole blood from HIV-infected individuals under antiretroviral treatment. No commercially-available assay can yet detect latent HIV-1-infected cells in 20-30 mL of whole blood from HIV-infected individuals under antiretroviral treatment. Assays available for research-only purposes can detect 1-30 latent HIV-1-infected cells per $10^6$ white blood cells in peripheral blood, but only after lengthy and repeated activation over a period of 1-3 weeks. Thus, HIV-1 qLDR offers a significant improvement in sensitivity over latent HIV assays. Moreover, no absolute quantitative standard yet exists for RNA assays, but the present disclosure provides compositions and methods capable of producing such an absolute quantitative standard.

In accordance with the description, a fluorogenic nucleic acid composition for quantitative detection of a target RNA sequence in a test sample comprises at least one pair of oligonucleotide probes with an upstream first probe and a downstream second probe complementary to and capable of specifically binding the target RNA in an upstream and downstream portion of the target RNA, respectively, wherein the at least one pair of oligonucleotide probes bind to a target RNA, wherein both probes are covalently bound to a nonfluorescent moiety, wherein the nonfluorescent moiety bound to the first probe chemically reacts with the nonfluorescent moiety on the second probe to form a fluorescent moiety covalently connecting the two probes when both probes of the probe set hybridize to the target RNA sequence; and wherein quantitative detection of target RNA may be performed by detecting the fluorescent signal generated.

In some embodiments, the target RNA sequence is HIV-1, HIV-2, Ebola hemorrhagic fever, SARS, influenza, hepatitis C, West Nile, polio, measles, CMV, Herpes, or Zika virus. In some embodiments, the composition comprises more than one pair of oligonucleotide probes. In some embodiments, the fluorogenic nucleic acid composition quantitatively detects 2 kb spliced HIV-1 RNA. In some embodiments, the fluorogenic nucleic acid composition quantitatively detects 4 kb spliced and 9 kB full-length HIV-1 RNA. In some embodiments, the fluorogenic nucleic acid composition quantitatively detects 9 kb full-length HIV-1 RNA.

In some modes, at least one pair of oligonucleotide probes comprises: SEQ ID NO: 1 and 2; SEQ ID NO: 3 and 4; SEQ ID NO: 5 and 6; SEQ ID NO: 7 and 8; SEQ ID NO: 9 and 10; SEQ ID NO: 11 and 12; and/or any pair of oligonucleotide probes that vary by one or two nucleotides per probe from any of the pairs recited in (a)-(f).

In some modes, the composition comprises more than one pair of oligonucleotide probes.

In some embodiments, the fluorogenic nucleic acid composition quantitatively detects spliced CD4+ RNA. In some embodiments, the binding of the probes to the target RNA creates a gap between the probes. In some embodiments, if the target RNA is linear, the upstream and downstream portions of the target RNA sequence have a gap of up to 8 nucleotides corresponding to the gap between the probes. There may also be no gap between the probes. In some embodiments, the nonfluorescent moiety is bound to the downstream end of the upstream first probe and wherein the nonfluorescent moiety is bound to the upstream end of the downstream second probe.

In some embodiments, at least one of the oligonucleotide probes comprise modified-backbone nucleotides. In some embodiments, the at least one modified-backbone oligonucleotide probe comprises protein nucleic acids (PNA), bridged nucleic acids (BNA), locked nucleic acids (LNA), and/or guanidine-modified PNA (GPNA). In some embodiments, both probes in a pair comprise modified-backbone nucleotides. In some embodiments, two probes in a pair comprise different types of modified-backbone nucleotides. In some embodiments, one probe in a pair comprises modified-backbone nucleotides. In some embodiments, both probes in a pair comprise solely oligonucleotides.

In some embodiments, the oligonucleotide probes are from 5 to 30 oligonucleotides long or from 18 to 21 oligonucleotides long. In some embodiments, the fluorescent moiety formed comprises any one of the fluorescent dyes provided in Table 3.

A fluorogenic method for quantitative detection of a target ribonucleic acid (RNA) sequence in a sample may comprise: adding to the sample a fluorogenic nucleic acid composition comprising at least one pair of oligonucleotide probes with an upstream first probe and a downstream second probe complementary to and capable of specifically binding the target RNA in an upstream and downstream portion of the target RNA, respectively, wherein the at least one pair of the probes binds to a target RNA, both probes are covalently bound to a nonfluorescent moiety, and the nonfluorescent moiety bound to the first probe chemically reacts with the nonfluorescent moiety on the second probe to form a fluorescent moiety covalently connecting the two probes when both probes of the probe set hybridize to the target nucleic acid sequence; optionally exposing the sample to denaturing conditions; hybridizing the probes in the fluorogenic nucleic acid composition; and detecting the amount of fluorescence emitted by the fluorescent moiety covalently connecting the two probes when both probes of the probe set hybridize to the target nucleic acid sequence and the probe nonfluorescent moieties react to produce the fluorescent product.

In some embodiments, the fluorogenic nucleic composition added to the sample is any of the fluorogenic nucleic acid compositions disclosed herein.

In some embodiments, the sample is exposed to denaturing conditions. In some embodiments, the denaturing conditions comprise temperature of from 50-100° C. and/or chemical denaturants. In some embodiments, the hybridizing of the probes occurs at a temperature of from 35° C. to 70° C. In some embodiments, the hybridizing of the probes occurs at isothermal conditions. In some embodiments, the hybridizing of the probes occurs during thermocycling conditions.

In some embodiments, the method further comprises normalizing the amount of fluorescence that is detected to the amount of fluorescence that is detected in a negative control sample that contains a non-target RNA sequence. In some embodiments, the method further comprises normalizing the amount of fluorescence that is detected to the amount of fluorescence that is detected in a positive control sample that contains a target RNA sequence of known concentration. In some embodiments, the method further comprises calculating the amount of each target RNA sequence in the test sample from the normalized amount of fluorescence detected.

In some embodiments, the first and second probes are each at a concentration of from 10 pM to 100 nM when mixed with the sample and in the reaction conditions.

In some embodiments, the test sample comprises mixed RNA species from cells. In some embodiments, the test sample is chosen from peripheral blood; lymph node; oral mucosa; gingival crevicular fluid (GCF); gut-associated lymphatic tissue (GALT); cerebrospinal fluid (CSF); central nervous system (CNS) tissue, including brain tissue; a mixed oral sample comprising oral mucosa, GCF, and saliva; and urine. In some embodiments, the method can detect a target sequence in single-stranded RNA. In some embodiments, the method can detect a target sequence in an RNA hairpin or an RNA pseudoknot or other RNA secondary, tertiary, or quaternary structure. In some embodiments, the method can detect a target sequence so as to identify the presence or absence of a mutation in RNA or an RNA splicing product. In some embodiments, the method can detect a target sequence with less than or equal to 5% variation in the target sequence.

In some embodiments, the method further comprises administering an anti-HIV medication to a patient and performing the fluorogenic method on samples obtained from the patient before and after the medication was administered. In some embodiments, the anti-HIV medication is undergoing clinical trials. In some embodiments, the method is conducted to determine if the patient's HIV strain(s) are susceptible to the anti-HIV medication. In some embodiments, the sample is obtained from the patient and an anti-HIV medication is administered to the patient if the patient is found to have a latent HIV reservoir.

In some embodiments, a test kit for quantitative detection of cell-associated HIV-1 RNA in a test sample comprises the fluorogenic nucleic acid composition described herein and at least one buffer. In some embodiments, the at least one buffer is a reaction buffer. In some embodiments, the reaction buffer comprises sodium chloride (NaCl) and potassium phosphate ($K_2HPO_4$). In some embodiments, the reaction buffer at final concentration comprises from 100 mM to 150 mM NaCl and from 5 mM to 15 mM $K_2HPO_4$. In some embodiments, the reaction buffer at final concentration comprises 10 mM $K_2HPO_4$ and has a pH of 7.4. In some embodiments, the test kit comprises at least one pair of fluorogenic probes to quantitatively detect spliced CD4+ RNA. In some embodiments, the test kit comprises a positive control. In some embodiments, the test kit comprises a negative control. In some embodiments, the negative control comprises a non-target RNA sequence.

Additional objects and advantages will be set forth in part in the description which follows, and in part will be obvious from the description, or may be learned by practice. The objects and advantages will be realized and attained by means of the elements and combinations particularly pointed out in the appended claims.

It is to be understood that both the foregoing general description and the following detailed description are exemplary and explanatory only and are not restrictive of the claims.

The accompanying drawings, which are incorporated in and constitute a part of this specification, illustrate one (several) embodiment(s) and together with the description, serve to explain the principles described herein.

BRIEF DESCRIPTION OF THE DRAWINGS

FIGS. 2a-d show fluorophore chemical structures and RNA structures. Molecular Interactions of Fluorophores in qLDR Compositions. (FIG. 2a.) Diagram of the chemical structure of an exemplary composition in which nonfluorescent reactive moieties (104 and 105) are attached to paired probes (101 and 102) of a probe set hybridized to a complementary target ribonucleic acid sequence (103). Once hybridized, the close proximate positions of the probe set nonfluorescent reactive moieties allows those moieties to bond covalently, producing a fluorescent reaction product (106) whose fluorescence can be quantitatively detected. (FIG. 2a.) Example of nonfluorescent reactive moieties for attachment to oligonucleotide or modified-backbone oligonucleotide primers (FIG. 2b-d). Target RNA templated autoligation of Ald-1 (104) and Ind (105) will create Cy3 and of Ald-2 (107) and Ind (105) will create Cy5, for the examples shown, through an aldol-type reaction.

FIG. 3a-m show RNA structures and possible probe binding configurations. These include linear RNA, RNA hairpin stem-loop, and RNA pseudoknot structures on target ribonucleic acid sequence (103) with possible, noninclusive probe binding configurations (101 and 102) to form the fluorescent product (106).

FIG. 10*a* shows latent HIV-infected cells and HIV negative cells (control), while FIG. 10*b* shows active HIV-infected cells.

DETAILED DESCRIPTION

Figures 1A, 1B:
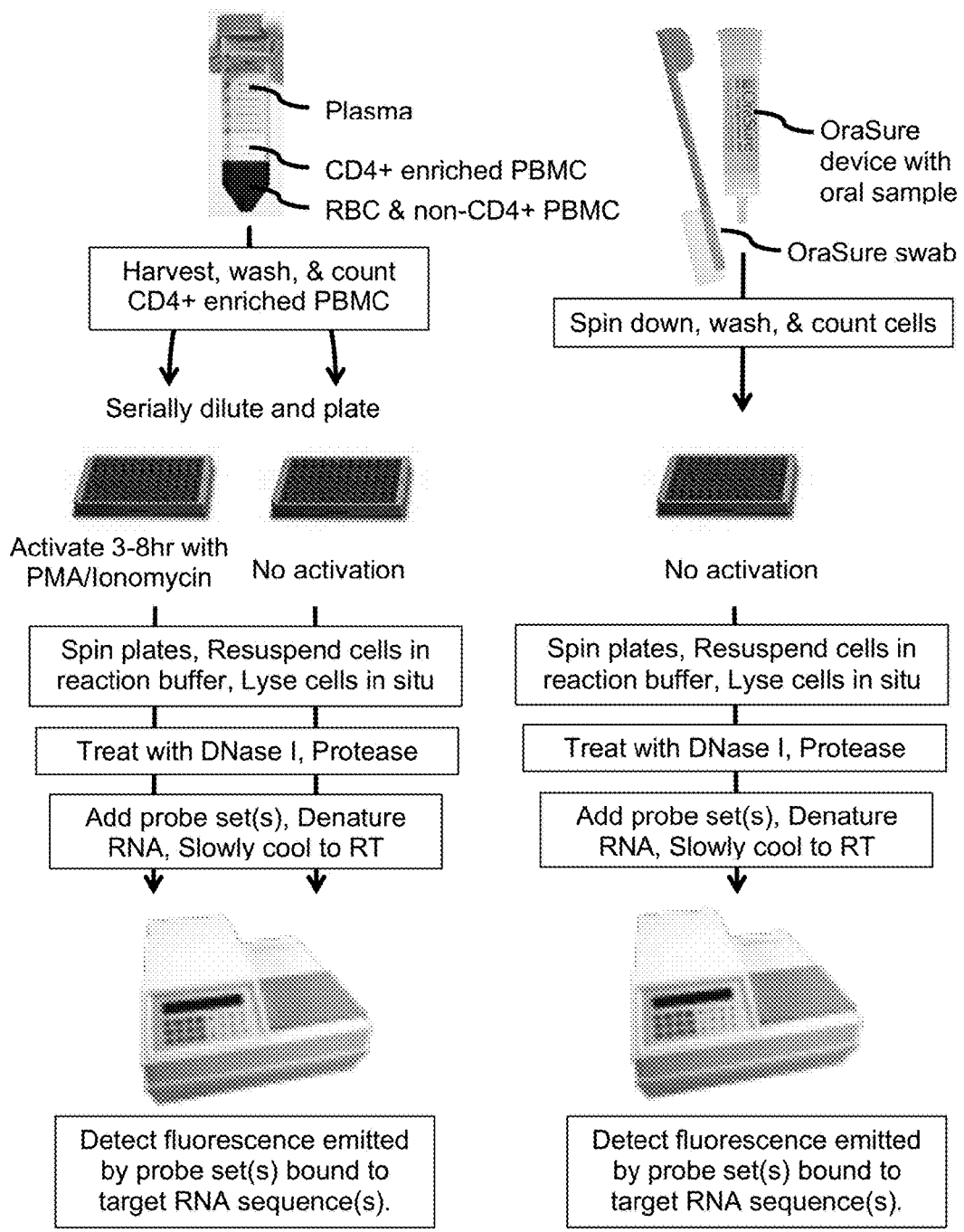
FIGS. 1a-b show quantitative Detection (singleplex or multiplex) of cell-based HIV-1 RNA in Samples by qLDR. Schematic of process, showing quantitative detection of cell-based HIV-1 RNA from blood (FIG. 1a) and mucosal (FIG. 1b) test samples, using qLDR technology.
Figure 4:
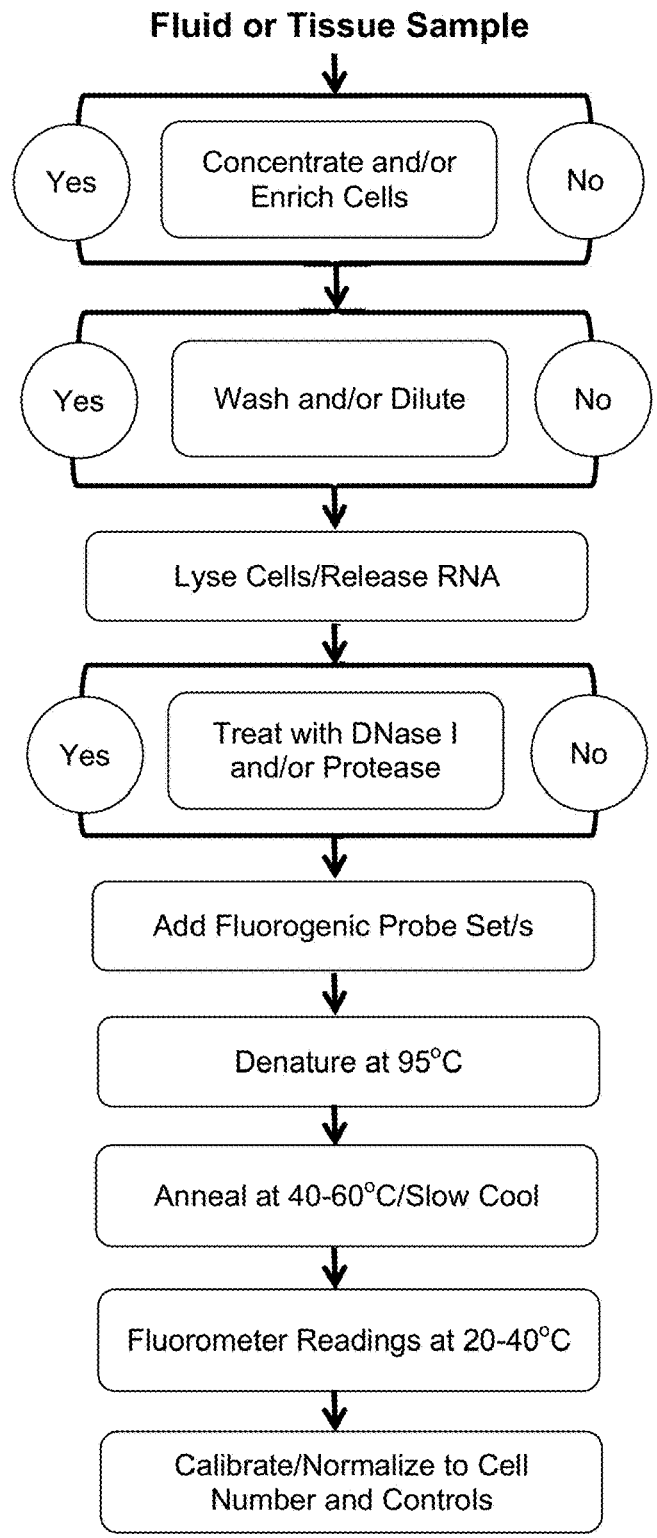
FIG. 4 provides a process flow diagram. General overview of a qLDR assay procedure for application to quantitative detection of RNA species from a fluid or tissue test sample. Optional steps are indicated as decision trees.

The application provides novel, quantitative, spliced-site containing, stem-loop containing, and other RNA target sequence detection technology, including compositions, reagents, methods, assays, and kits, which employ tagged, probe-set pairs of sequences that bridge particular RNA sequences, to provide highly-precise and accurate quantitation of the levels of a nucleic acid target sequence present in a test sample. We call this technology quantitative ligation detection reaction (qLDR) technology. qLDR can be performed isothermally or through thermocycling, and yields results within 15 min-3 hr, excluding sample preparation time.

In some embodiments, target RNA sequences are detected through a fluorogenic chemical reaction that takes place, in some embodiments and not including background, when and only when the probes proximally interact across an RNA spliced site, yielding a highly-specific, sequence-dependent reaction with fluorescent read-out directly at the RNA level. With fluorescence detection over time and co-detection of cellular spliced control RNAs, qLDR allows real-time quantitation of RNA levels in a broad range of biologically-relevant contexts.

The compositions, reagents, methods, assays, and kits overcome the limitations in the prior art to accurately and sensitively quantitate latent reservoirs of HIV—infected cells in HAART patients. HIV qLDR utilizes two probes to bind to complementary ribonucleic acid sequences on an HIV RNA conserved primary sequence or secondary structure, providing resulting fluorogenic detection down to one (1) latently infected HIV cell in $10^6$ CD4+ T cells isolated from 20-30 mL of peripheral blood.

The improved, RNA qLDR-based compositions, reagents, methods, assays, and kits answer a critical need for highly-specific and sensitive detection of spliced HIV mRNA purified from peripheral blood CD4+ cells isolated from HAART/cART patients, which may successfully be deployed in the development and evaluation of new treatments for HIV AIDS, including cure treatments.

The present compositions and methods can also be used to detect other RNA targets in biological systems.

Some embodiments may be used in principle to quantitatively detect a broad range of ribonucleic acid target sequences, and is particularly suitable, for example, to quantitatively detect RNA spliced sites, quantitatively differentiate alternatively spliced forms, or differentially detect RNA in a mixed RNA-DNA sample, such as in a live cell or in samples also containing DNA. Some embodiments are further useful for detecting sequence variants of a target sequence, including single nucleotide polymorphisms (SNP), insertions, deletions, repeats, as well as across short deletions or insertions of up to four bases at the ligation point of the target sequence. Some embodiments are also useful for detection of RNA hairpins, pseudoknots, and other RNA secondary, tertiary, and quaternary structures (FIG. 3*a-m*). Detection specificity is facilitated by the use of short, stabilized probes. Such length allows detection of even short, conserved regions within otherwise poorly conserved sequences, particularly in the genomes of RNA viruses.

The invention further has broad applicability to the quantitative detection of spliced RNA associated with active or latent viral infection, genetic disease, cancer, as well as for gene fusion and other mutation detection events. Embodiments are suitable for use in point-of-care or high throughput diagnostic devices, including, by way of example, detection in oral and other mucosa, lymphatic tissue, central nervous system (CNS) tissue including brain, cerebrospinal fluid (CSF), GALT, blood, urine, semen, sputum, tears and other bodily fluids and tissues. Suitable detection platforms include, without limitation, microarrays, in situ detection in tissues or cells, and microfluidic detection. Detection paradigms include, without limitation, quantitative and staging diagnosis, definitive diagnosis, and point-of-care diagnosis of acute and latent viral and bacterial infections, cancers, and genetic diseases.

The embodiments herein have additional value within the HIV research field to elucidate the relationship between production of full-length spliced RNA and virus production by latent and activated cells, data critically needed in the efforts to discover a cure to HIV infection. The embodiments herein further can be used for detection of RNA-specific structures involved in other diseases, cell regulation and development, and across populations allowing for quantitative, structural determinations of functionally important RNA molecules and how they change as a function of time and conditions. The embodiments herein can also be used for in vivo and in situ detection and quantification of variant RNAs or RNA secondary structures, and the like.

In some embodiments, the technology does not involve conversion of RNA to DNA, unlike RT-PCR, and thus does not lose representation of RNA present in the reaction, nor does it suffer from the addition of mutations which occurs during RT-PCR.

I. Fluorogenic Nucleic Acid Composition

A fluorogenic nucleic acid composition for quantitative detection of a target RNA sequence in a test sample may comprise at least one pair of oligonucleotide probes with an upstream first probe and a downstream second probe complementary to and capable of specifically binding the target RNA in an upstream and downstream portion of the target RNA, respectively, wherein the at least one pair of oligonucleotide probes bind to a target RNA, wherein both probes are covalently bound to a nonfluorescent moiety, wherein the nonfluorescent moiety bound to the first probe chemically reacts with the nonfluorescent moiety on the second probe to form a fluorescent moiety covalently connecting the two probes when both probes of the probe set hybridize to the target RNA sequence; and wherein quantitative detection of target RNA may be performed by detecting the fluorescent signal generated.

Thus, the composition employs at least one pair of oligonucleotide probes where each probe in the pair comprises a nonfluorescent moiety, wherein the first probe comprises a first nonfluorescent moiety and the second probe comprises a second nonfluorescent moiety. When the probes come sufficiently close, the two nonfluorescent moieties react to create a covalently-bound fluorescent moiety.

Embodiments in which target RNA sequences contain an RNA spliced site may thus further be characterized as embodiments of fluorogenic composition wherein the upstream and downstream portions of the target RNA sequence span an RNA spliced site, with a distance between the probes of 0-8 nucleotides on a linear RNA or a gap consisting of the RNA sequence within a nonlinear structure. Likewise, embodiments in which target RNA sequences contain an RNA hairpin stem-loop may thus further be characterized as embodiments of fluorogenic composition wherein the upstream and downstream portions of the target RNA sequence are on either side of (span) or within a hairpin stem-loop, with a gap between the probes consisting of the RNA sequence within the nonlinear structure. Similarly, embodiments in which target RNA sequences contain other RNA secondary structure, such as quadruplex structure, knots, pseudoknots, and the like may thus further be characterized as embodiments of fluorogenic composition wherein the upstream and downstream portions of the target RNA sequence are within or on either side of (span) such a structure, with a gap between the probes consisting of the RNA sequence within the nonlinear structure (FIG. 3a-m).

A. Oligonucleotide Probes

The fluorogenic nucleic acid composition comprises at least one pair of oligonucleotide probes. In some instances, the fluorogenic nucleic acid composition may comprise more than one pair of oligonucleotide probes.

1. Types of Oligonucleotide Probes

The probe sequences can be composed of oligonucleotides or modified backbones, including but not limited to PNA and LNA, as well as a mixture of oligonucleotide and modified backbone sequences within the same probe or between probes in a fluorogenic probe set.

A single probe may comprise of a protein nucleic acid (PNA) probe tethered to a nonfluorescent reactive moiety or an oligonucleotide primer tethered to a nonfluorescent reactive moiety at either the 5' or 3' end. The PNA or oligonucleotide based probe sets can be used as homogenous or heterologous probe sets. Although the homologous (PNA-PNA probe set or oligonucleotide-oligonucleotide) probe sets may be used, modified-backbone oligonucleotides suitable for use as probe sets also include, without limitation, bridged nucleic acids (BNA), locked nucleic acids (LNA), and guanidine-modified PNA (GPNA), and other modifications of the PNA backbone. Heterologous probe sets may also be used.

In some embodiments, at least one of the oligonucleotide probes are modified-backbone oligonucleotide probes. In some embodiments, the at least one modified-backbone oligonucleotide probe comprises protein nucleic acid (PNA) probes, bridged nucleic acids (BNA), locked nucleic acids (LNA), and guanidine-modified PNA (GPNA).

In some embodiments, both probes in a pair comprise modified-backbone nucleotides. In some embodiments, the two probes in a pair comprise different types of modified-backbone nucleotides.

In some embodiments, one probe in a pair comprises modified-backbone oligonucleotides. In some embodiments, some of the nucleotides in a probe are modified-backbone nucleotides and others are unmodified.

In some embodiments, the oligonucleotide probes are from 5 to 30 oligonucleotides long or from 18 to 21 oligonucleotides long.

2. Sequence Design of Oligonucleotide Probes

The sequence design of oligonucleotide probes may be based on the sequence of the target of interest. To design sequences for fluorogenic probes for detection of nonlinear RNA sequences, the following protocol should may employed:

First, if the RNA sequence is known to contain certain stable secondary structures, complementary sequences may be chosen to the 5' and 3' regions on either side of the secondary structure, such as shown for a hairpin and a pseudoknot in FIG. 3a-m. Alternatively, as shown in FIG. 3a-m, the probe sequences may be complementary to sequences within the hairpin, including within any bulge elements and the complementary bases within the stem of the hairpin. If PNA-based probes are used, the PNA is able to enter into stable triplex interactions within the stem of the hairpin, a process facilitated by partial denaturation and return to the annealing temperature of the structure.

Second, if the nonlinear structures of an RNA sequence have not previously been identified, the thermodynamically stable nonlinear structure of the RNA sequence may be mapped using online software programs using a dynamic programming algorithm based on free energy calculations that are widely used to search for RNA nonlinear structures. In some instances, the most thermodynamically stable structure may be chosen. These programs can be augmented by additional calculations based on experimental determinations. After mapping of the likely secondary structures, probe sequences may be chosen as described in the immediately preceding paragraph for hairpins, pseudoknots, and other RNA secondary structures.

In some embodiments, the variation tolerated depends on the sequence length and probe backbone, with greater variation tolerated for longer sequences and modified probe backbones. A probe sequence length of 10 bases or less can tolerate a 1-2 base variation, while a sequence length of 11-20 bases can tolerate up to a 6 base variation, and a sequence length of 21 or greater bases can tolerate a 7 and greater base variation. Thus, variation in probe sequences may occur at 1, 2, 3, 4, 5, 6, 7, 8, or 9 bases, or higher as compared to sequences provided herein and as compared to the exact complement in a target sequence. Probes degenerate at particular positions may also be used to allow for specific binding to more than one sequence variant.

Thus, in some embodiments, the base sequence of each probe in a probe set may be perfectly complementary or partially complementary to a target sequence of the template, and may include degenerate sequence to allow for template sequence variation. In some embodiments, allowable sequence variation is 5%. The use of probe sequences in the range of 5-30 or 5-40mers may be used in order to maximize efficiency and multiplex detection. Multiple sets of different probes, each complementary to a different target sequence, within one or more of the same or different RNA templates, may be used in the same or tandem reactions for multiplex detection of target sequences. Probes shorter in length than 5mers or longer in length than 40mers may not be appropriate in all embodiments. In some embodiments, probes from 5-30mers may be used.

3. Targets for Oligonucleotide Probes

The oligonucleotide probes may bind to different RNA sequences, depending on what an operator wishes to detect. In other words, the disclosure more broadly can be applied to quantitative detection of levels of target RNA sequences in a variety of research and clinical contexts.

The oligonucleotide probes may be chosen to bind to an RNA virus or a retrovirus. In some embodiments, the target RNA sequence is HIV-1, HIV-2, Ebola hemorrhagic fever, SARS, influenza (including but not limited to influenza A), hepatitis C, West Nile, polio, measles, CMV, Herpes, or Zika virus. Compositions, reagents, methods, assays, and kits for use in research, diagnostic, and clinical applications are provided to quantitate viral infection levels of other viruses, particularly RNA viruses such as other Human immunodeficiency viruses (e.g., HIV-2), Zika virus, Hepatitis C virus, Herpes viruses, Cytomegalovirus (CMV), SARS virus, Norwalk virus, West Nile virus, Yellow Fever virus, Dengue viruses, and other flavi- and coronaviruses; Lassa virus, Rift Valley fever virus, Chikungunya virus, Influenza A virus, Hantavirus, Marburg virus, Ebola virus, Nipah virus, Rubella virus, Canine Influenza virus, HoBi-like pestivirus, Schmallenberg virus, Simian immunodeficiency virus (SIV), Powassan virus, Hepatitis E virus, Canine hepacivirus, Colorado tick fever virus, or Theiler's disease associated virus; as well as to quantitate levels of RNA sequences generally, and spliced RNA and RNA secondary structures more particularly, in a broad range of disease, developmental, structural, epidemiological, and evolutionary contexts.

RNA targets other than viruses may also be detected. RNA levels in cells that are of interest may also be targeted. For example, techniques herein can also be used in prostate cancer diagnosis and treatment monitoring. Prostate cancer (PCa) is the leading cancer diagnosis for men in the U.S., with a death rate second only to lung cancer for this demographic. Aggressive PCa (termed CRPC) is the result of a switch to androgen-independence, mediated by alternative splicing or other genetic change that removes the androgen-binding domain of the androgen receptor (AR) in prostate cells. The prostate cells are then no longer dependent on androgens for stimulation of growth. With an average life expectancy of 19 months after CRPC diagnosis, there is a critical need for sensitive assays to detect the alternatively spliced versions of the androgen receptor RNA for early diagnosis. PCa drugs in development target AR splice variants or its transcriptional targets, highlighting a great need for companion diagnostics to identify the production of AR splice variants. The developments described herein can meet this need and can be used to directly detect the RNA spliced sites of the two most commonly arising CRPC AR splice variants, ARv7 and ARv567es, which result in deletions of the AR ligand binding domain. This provides highly sensitive and specific detection in biopsy, circulating tumor cells (CTCs), blood or urine of PCa.

Other applications include spliced RNAs, microRNAs (miRNA) and long noncoding RNAs (lncRNA) indicative of medically important conditions. A nonexhaustive list of examples of spliced sites or RNA level targets implicated in disease is provided in Table 1. Any RNA of interest may be detected using this composition and method.

TABLE 1

Spliced sites or RNA level targets implicated in disease

| Gene | Diseases/Conditions | Relevant Spliced Sites |
|---|---|---|
| CD46 | Immune deficiency, multiple sclerosis, rheumatoid arthritis, asthma, cancer, Neisseria bacteria infection, Measles virus | Spliced sites including or excluding Exons 7, 8, 9, 13, 14 |
| Klotho | Premature aging, chronic kidney disease | Transmembrane form with spliced Exons 3-4, 4-5, and lacking intron region following Exon 3 |
| DENND1A | Polycystic ovary syndrome | Variant 2 (V2) |
| BC200 lncRNA | Breast cancer | Higher BC200 level |
| DN RBFOX2 | Diabetic cardiomyopathy | Dominant negative (DN) isoform |
| SF3B1 | Myelodysplastic syndromes | Cryptic 3' spliced site usage |
| BRCA1 | Resistance to PARP Inhibition and Cisplatin | BRCA1-Δ11q |
| ITGB4, PYCR1 | Non-Small Cell Lung Cancer | Splice variants of ITGB4, PYCR1 |
| CD44 | Melanoma | CD44v8-10 |

4. HIV-1 Probes

Particular HIV-1 probes are included herein. In some embodiments, the composition quantitatively detects 2 kb spliced HIV-1 RNA. In some embodiments, the composition quantitatively detects 4 kb spliced and 9 kb full length HIV-1 RNA. In some embodiments, the composition quantitatively detects 9 kb full-length HIV-1 RNA. In some embodiments, the composition quantitatively detects spliced CD4+ RNA.

In some embodiments, probes may be chosen from Table 2.

TABLE 2

Latent HIV-1 qLDR Probes

| SEQ ID NO: | Sequence* (5'→3') | Reactive Moiety[a] | Site[b] | Target Region[b] (HIV-1 Gene) | HIV-1 RNA Detected[c] |
|---|---|---|---|---|---|
| 1 | *CCTGTATCTAATAGAGC | Ald-1 | 2332-2316 | 2110-2550 (pol/protease) | Full length (9 kb) |
| 2 | TCTAATACTGTATCATCT* | Ind | 2353-2336 | | |
| 3 | *TTGTACTGTGCTGACA | Ald-2 | 6962-6947 | 6740-7190 (gp160/120) | Spliced (4 kb) Full-length (9 kb) |
| 4 | GCCTAATTCCATGTGT* | Ind | 6981-6966 | | |

TABLE 2-continued

Latent HIV-1 qLDR Probes

| SEQ ID NO: | Sequence* (5'→3') | Reactive Moiety[a] | Site[b] | Target Region[b] (HIV-1 Gene) | HIV-1 RNA Detected[c] |
|---|---|---|---|---|---|
| 5 | *ATAGTGCTTCCTGCT | Ald-2 | 7813-7799 | 7590-8030 | Spliced |
| 6 | GTCATTGAGGCTGCG* | Ind | 7831-7817 | (gp160/41) | (4 kb) Full-length (9 kb) |
| 7 | *GAAGAGGCACAGGCTC | Ald-1 | 8522-8507 | 8300-8750 | Spliced |
| 8 | TCTCAAGCGGTGGTA* | Ind | 8540-8526 | (env) | (2 kb, 4 kb) Full-length (9 kb) |
| 9 | *CTTTG[d] | Ald-1 | 6043-6039 | 5820-8590 | Spliced |
| 10 | TGGGT*[e] | Ind | 8383-8379 | (tat-rev) | (2 kb) |
| 11 | *CTYTGRTABARRADY | Ald-1 | 6043-6029 | 5820-8590 | Spliced |
| 12 | NNBNKGGRDRNGGRT* | Ind | 8393-8379 | (tat-rev) | (2 kb) |
| 13 | *CTCTGGGCTTG | Ald-1 | 455-465 | CD4-1-5' | CD4 |
| 14 | GAAATGGCAGGG* | Ind | 10880-10869 | CD4-1-3' | Spliced-1 |
| 15 | *CCAGTTGCAGCA | Ald-2 | 10983-10972 | CD4-2-5' | CD4 |
| 16 | CTGGGAGGAGCG* | Ind | 11102-11091 | CD4-2-3' | Spliced-2 |

*Fluorogenic probe moiety attachment position on probe sequence.
[a]Fluorogenic probe moiety structures as tested below. Ald-1, Ald-2, or an alternative Ald may be at any Ald position.
[b]HIV Sequence Database Compendium 2015, HIV-1 HXB2 sequence numbering system (hiv.lanl.gov). Target region also includes rearrangements of these sequences that may occur through mutation, splicing or selection. Probe may be either fully homologous or a consensus homolog to the reverse complement within target region.
[c]HIV-1 fragment lengths are approximate.
[d]PNA: 5' Ald-CTTTG-DMLys-DMLys-CONH$_2$.
[e]PNA: 3' Ind-TGGGT-DMLys-DMLys-CONH$_2$.

For example, in some embodiments, wherein at least one pair of oligonucleotide probes may comprise: (a) SEQ ID NO: 1 and 2; (b) SEQ ID NO: 3 and 4; (c) SEQ ID NO: 5 and 6; (d) SEQ ID NO: 7 and 8; (e) SEQ ID NO: 9 and 10; (f) SEQ ID NO: 11 and 12; (g) SEQ ID NO: 13 and 14; (h) SEQ ID NO: 15 and 16; and/or (i) any pair of oligonucleotide probes that vary by one, two, or more nucleotides per probe from any of the pairs recited in (a)-(h). SEQ ID NO: 9 and 10 are shown as PNA probes, but either unmodified or PNA versions of these probes may be used. Short probes may lend themselves to PNA modification, which allows for tighter binding (high sensitivity) due to lack of a charged backbone and high specificity due to shorter length.

In some embodiments, the variation tolerated depends on the sequence length and probe backbone, with greater variation tolerated for longer sequences and modified probe backbones. A probe sequence length of 10 bases or less can tolerate a 1-2 base variation, while a sequence length of 11-20 bases can tolerate up to a 6 base variation, and a sequence length of 21 or greater bases can tolerate a 7 and greater base variation. Thus, variation in probe sequences may occur at 1, 2, 3, 4, 5, 6, 7, 8, or 9 bases, or higher as compared to sequences provided herein and as compared to the exact complement in a target sequence. Probes degenerate at particular positions may also be used to allow for specific binding to more than one sequence variant.

5. Spatial Arrangement of the Probes

Sequences for the probes may be chosen to create a spatial arrangement of the probes that allows for binding between the two nonfluorescent moieties in order to form a fluorescent moiety covalently connecting the two probes when both probes of the probe set hybridize to the target RNA sequence.

In some embodiments, if the target RNA is linear, the upstream and downstream portions of the target RNA sequence may be contiguous (with no gap) or have a gap of from 1-8 nucleotides corresponding to the gap between the probes.

In some embodiments, the first nonfluorescent moiety is bound to the downstream end of the upstream first probe and the second nonfluorescent moiety is bound to the upstream end of the downstream second probe.

B. Nonfluorescent Moiety and Fluorophores

Each of the probes may be covalently bound to a nonfluorescent moiety. When the two probes in a pair are within a close enough proximity, the nonfluorescent moieties on each probe are capable of reacting to produce a fluorophore and hence a fluorescent signal under the right conditions. In other words, one probe has a first nonfluorescent moiety and the other probe in a pair has a second nonfluorescent moiety. The first and second nonfluorescent moieties bind to create a fluorophore.

Suitable fluorogenic dyes useful as fluorophores include, without limitation, Cy2, 3, 5, 7, 3b, 3.5, 5.5, 7.5, sulfoCy derivatives, Quasar® dyes, and any of the applicable dyes listed in Table 3. In one embodiment, the nonfluorescent reactive moieties may have an indole aldehyde and an indolene, respectively, as shown in FIG. 2a-d for the fluorogenic reactions that would produce Cy3 (Ald-1) and Cy5 (Ald-2) as examples.

Table 3 provides a list of additional fluorophores which may be suitable for qLDR. Fluorophores are fluorescent due to their aromatic chemical structures; these aromatic structures lend themselves to the reaction of reactive fluorogenic dye moieties through aldol-type and other reactions, including conjugation addition of enols. The mechanism of reaction for the reactive fluorogenic moieties on the ends of the fluorogenic probes may be through nucleophilic attack of an indolene to an aldehyde (aldol-type reaction) Similarly, an enolate or enol equivalent can be added to an α,β-unsaturated carbonyl compound, through conjugate addition. In one possible enol conjugation mechanism, the reaction of an enolate with an aldehyde follows a reaction progression of (a) enolization, (b) aldol addition, and (c) dehydration, to yield the final covalently-bonded fluorescent product. The reaction can be acid- or base-catalyzed, but may also occur at neutral pH. However, other possible fluorogenic reactions include Diels-Alder and similar synthesis mechanisms for aromatic ring formation or the use of a reactive halide moiety. Such reactions can yield symmetrical or nonsymmetrical fluorescent products.

The utility of reactive fluorogenic moieties can be quickly determined by mixing the moieties at different molar concentrations with equal stoichiometry. The higher concentrations of the fluorogenic moieties in free solution drive the reaction by mass action, mimicking the effect of an oligonucleotide-templated reaction in which the dye halves are brought together in close proximity by probes hybridizing to an oligonucleotide template. The lower the concentration needed, the better the reaction efficiency; however, a very low concentration yielding fluorescence will likely result in prohibitively high background fluorescence. Thus, an ideal reaction concentration for the unattached fluorogenic moieties is above the molar concentration of the probes to be used in the reaction yet low enough for the reaction to occur with high yield; that is, generally, the free reaction concentration for product formation should typically be above 1 pM-1 µM and below 1-100 mM. The pH of the reaction is determined by the optimal reaction yield with the least breakdown of reactants and the lowest background fluorescence, generally with a pH from 4-11. The salinity of the reaction may be important for fluorescence, with a lower level of 50-100 mM generally required for simultaneous or sequential fluorescence detection of the reaction.

TABLE 3

| Applicable Fluorescent Dyes | | |
|---|---|---|
| Cyanine 2 | Cascade Yellow antibody conjugate pH 8.0 | Magnesium Orange |
| 1-Anilinonaphthalene-8-sulfonic acid (1,8-ANS) | CFDA | Marina Blue |
| 1,8-ANS (1-Anilinonaphthalene-8-sulfonic acid) | CI-NERF pH 2.5 | mBanana |
| 5-(and-6)-Carboxy-2',7'-dichlorofluorescein pH 9.0 | CI-NERF pH 6.0 | mCherry |
| 5-FAM pH 9.0 | Citrine | mHoneydew |
| 5-ROX (5-Carboxy-X-rhodamine, triethylammonium salt) | Coumarin | MitoTracker Green |
| 5-ROX pH 7.0 | Coumarin 343 | MitoTracker Green FM, MeOH |
| 5-TAMRA | Cyanine 3 | MitoTracker Orange |
| 5-TAMRA pH 7.0 | Cyanine 3.5 | MitoTracker Orange, MeOH |
| 5-TAMRA-MeOH | Cyanine 5 | MitoTracker Red |
| 6 JOE | Cyanine 5.5 | MitoTracker Red, MeOH |
| 6-Carboxyrhodamine 6G pH 7.0 | Cyanine 7 | mOrange |
| 6-Carboxyrhodamine 6G, hydrochloride | Cyanine 7.5 | mPlum |
| 6-HEX, SE pH 9.0 | CyQUANT GR-DNA | mRFP |
| 6-TET, SE pH 9.0 | DansylCadaverine | mStrawberry |
| 6,8-Difluoro-7-hydroxy-4-methylcoumarin pH 9.0 | DansylCadaverine, MeOH | mTangerine |
| 7-Amino-4-methylcoumarin pH 7.0 | DAPI | NBD-X |
| 7-Hydroxy-4-methylcoumarin | DAPI-DNA | NBD-X, MeOH |
| 7-Hydroxy-4-methylcoumarin pH 9.0 | Dapoxyl (2-aminoethyl) sulfonamide | NeuroTrace 500/525, green fluorescent Nissl stain-RNA |
| Acridine Orange | DDAO pH 9.0 | Nile Blue, EtOH |
| Alexa 350 | Di-8 ANEPPS | Nile Red |
| Alexa 405 | Di-8-ANEPPS-lipid | Nile Red-lipid |
| Alexa 430 | DiI | Nissl |
| Alexa 488 | DiO | Oregon Green 488 |
| Alexa 532 | DM-NERF pH 7.0 | Oregon Green 488 antibody conjugate pH 8.0 |
| Alexa 546 | DsRed | Oregon Green 514 |
| Alexa 555 | DTAF | Oregon Green 514 antibody conjugate pH 8.0 |
| Alexa 568 | dTomato | Pacific Blue |
| Alexa 594 | DyLight 350 | Pacific Green |
| Alexa 647 | DyLight 405 | PEP |
| Alexa 660 | DyLight 488 | Perylene |
| Alexa 680 | DyLight 549 | Phycoerythrin |
| Alexa 700 | DyLight 594 | PicoGreendsDNA quantitation reagent |

TABLE 3-continued

Applicable Fluorescent Dyes

| | | |
|---|---|---|
| Alexa Fluor 430 antibody conjugate pH 7.2 | DyLight 633 | PO-PRO-1 |
| Alexa Fluor 488 antibody conjugate pH 8.0 | DyLight 649 | PO-PRO-1-DNA |
| Alexa Fluor 488 hydrazide-water | DyLight 680 | PO-PRO-3 |
| Alexa Fluor 532 antibody conjugate pH 7.2 | Eosin | PO-PRO-3-DNA |
| Alexa Fluor 555 antibody conjugate pH 7.2 | Eosin antibody conjugate pH 8.0 | POPO-1 |
| Alexa Fluor 568 antibody conjugate pH 7.2 | Erythrosin-5-isothiocyanate pH 9.0 | POPO-1-DNA |
| Alexa Fluor 610 R-phycoerythrin streptavidin pH 7.2 | Ethidium Bromide | POPO-3 |
| Alexa Fluor 647 antibody conjugate pH 7.2 | Ethidium homodimer-1-DNA | Propidium Iodide |
| Alexa Fluor 647 R-phycoerythrin streptavidin pH 7.2 | Ethidiumhomodimer | Propidium Iodide-DNA |
| Alexa Fluor 660 antibody conjugate pH 7.2 | evoglow-Bs1 | Pyrene |
| Alexa Fluor 680 antibody conjugate pH 7.2 | evoglow-Bs2 | R-Phycoerythrin pH 7.5 |
| Alexa Fluor 700 antibody conjugate pH 7.2 | evoglow-Pp1 | ReAsH |
| Allophycocyanin pH 7.5 | eYFP (Enhanced Yellow Fluorescent Protein) | Resorufin |
| AA4CA conjugate | FAM | Resorufin pH 9.0 |
| Amino Coumarin | FDA | Rhod-2 |
| APC (allophycocyanin) | FITC | Rhod-2 Ca2+ |
| Atto 647 | FITC antibody conjugate pH 8.0 | Rhodamine |
| Auramine O | Fluo-3 | Rhodamine 110 |
| BCECF pH 5.5 | Fluo-4 | Rhodamine 110 pH 7.0 |
| BCECF pH 9.0 | Fluor-Ruby | Rhodamine B |
| BDP 630/650 | Fluorescein | Rhodamine Green |
| BDP FL | Fluorescein 0.1M NaOH | Rhodamine Red-X antibody conjugate pH 8.0 |
| BDP R6G | Fluorescein antibody conjugate pH 8.0 | Rhodaminen Green pH 7.0 |
| BDP TMR | Fluorescein dextran pH 8.0 | Rhodaminephalloidin pH 7.0 |
| BDP TR | Fluorescein pH 9.0 | Rhodol Green antibody conjugate pH 8.0 |
| BFP (Blue Fluorescent Protein) | Fluoro-Emerald | ROX |
| BO-PRO-1-DNA | FM 1-43 | Sapphire |
| BO-PRO-3-DNA | FM 1-43 lipid | SBFI-Na+ |
| BOBO-1-DNA | FM 4-64 | Sodium Green Na+ |
| BOBO-3-DNA | FM 4-64, 2% CHAPS | Sulfo-Cyanine 3 |
| BODIPY 650/665-X, MeOH | Fura Red Ca2+ | Sulfo-Cyanine 5 |
| BODIPY FL conjugate | Fura Red, high Ca | Sulfo-Cyanine 5.5 |
| BODIPY FL, MeOH | Fura Red, low Ca | Sulfo-Cyanine 7 |
| Bodipy R6G SE | Fura-2 Ca2+sup | Sulforhodamine 101, EtOH |
| BODIPY R6G, MeOH | Fura-2, high Ca | SYBR Green I |
| BODIPY TMR-X antibody conjugate pH 7.2 | Fura-2, no Ca | SYPRO Ruby |
| Bodipy TMR-X conjugate | HcRed | SYTO 13-DNA |
| BODIPY TMR-X, MeOH | Hoechst 33258 | SYTO 45-DNA |
| BODIPY TMR-X, SE | Hoechst 33258-DNA | SYTOX Blue-DNA |
| BODIPY TR-X phallacidin pH 7.0 | Hoechst 33342 | TAMRA |
| BODIPY TR-X, MeOH | Indo-1 Ca2+ | Tetramethylrhodamine antibody conjugate pH 8.0 |
| BODIPY TR-X, SE | Indo-1, Ca free | Tetramethylrhodamine dextran pH 7.0 |
| BOPRO-1 | Indo-1, Ca saturated | Texas Red-X antibody conjugate pH 7.2 |
| BOPRO-3 | Indocyanine Green | TO-PRO-1-DNA |
| Calcein | JC-1 | TO-PRO-3-DNA |
| Calcein pH 9.0 | JC-1 pH 8.2 | TOTO-1-DNA |
| Calcium Crimson | Lissaminerhodamine | TOTO-3-DNA |
| Calcium Crimson Ca2+ | LOLO-1-DNA | TRITC |

TABLE 3-continued

| Applicable Fluorescent Dyes | | |
|---|---|---|
| Calcium Orange | Lucifer Yellow, CH | X-Rhod-1 Ca2+ |
| Calcium Orange Ca2+ | LysoSensor Yellow pH 3.0 | YO-PRO-1-DNA |
| Carboxynaphthofluorescein pH 10.0 | LysoSensor Yellow pH 9.0 | YO-PRO-3-DNA |
| Cascade Blue | LysoTracker Red | YOYO-1-DNA |
| Cascade Yellow | Magnesium Green Mg2+ | YOYO-3-DNA |

Nonfluorescent reactive moiety containing probes may be synthesized using the methods of Meguellati et al., DNA-templated synthesis of trimethine cyanine dyes: a versatile fluorogenic reaction for sensing G-quadruplex formation, Angew Chem. Int. Ed. Engl. 49:2738-2742 (2010). Alternatively, in a post synthetic chemical modification, a nonfluorescent reactive moiety (FIG. 2a-d, Ald or Ind) with a carboxylic acid functional group can be readily linked to oligonucleotide primer containing a 5' or 3' amino modifier. Either method can be used to produce probe sets.

II. Fluorogenic Methods for Quantitative Detection of RNA

In some embodiments, a fluorogenic method for quantitative detection of a target ribonucleic acid (RNA) sequence in a sample comprises: (a) adding to the sample a fluorogenic nucleic acid composition comprising at least one pair of oligonucleotide probes with an upstream first probe and a downstream second probe complementary to and capable of specifically binding the target RNA in an upstream and downstream portion of the target RNA, respectively, wherein (i) the at least one pair of oligonucleotide probes bind to a target RNA, (ii) both probes are covalently bound to a nonfluorescent moiety, and (iii) the nonfluorescent moiety bound to the first probe chemically reacts with the nonfluorescent moiety on the second probe to form a fluorescent moiety covalently connecting the two probes when both probes of the probe set hybridize to the target nucleic acid sequence; (b) optionally exposing the sample to denaturing conditions; (c) hybridizing the probes in the fluorogenic nucleic acid composition; and (d) detecting the amount of fluorescence emitted by the fluorescent moiety covalently connecting the two probes when both probes of the probe set hybridize to the target nucleic acid sequence.

The fluorogenic method may be conducted with any of the fluorogenic nucleic acid compositions described herein.

In some embodiments, the method can detect a target sequence in single-stranded RNA. In some embodiments, the method can detect a target sequence in an RNA hairpin or an RNA pseudoknot. In some embodiments, the method can detect a target sequence so as to identify the presence or absence of a mutation in RNA or an RNA splicing product. In some embodiments, the method can detect a target sequence with less than or equal to 5% variation in the target sequence.

A. Reaction Conditions

1. Probe Concentration and Reaction Buffers

In some embodiments, the first and second probes within the pair of probes are each at a concentration of from 10 pM to 100 nM when mixed with the sample and in the reaction conditions.

1. A person of ordinary skill in the art can supply reaction buffers for optionally denaturing the target RNA and performing the probe hybridization. In some embodiments, the reaction buffer comprises sodium chloride (NaCl) and potassium phosphate ($K_2HPO_4$). In some embodiments, the reaction buffer at final concentration comprises from 100 mM to 150 mM NaCl and from 5 mM to 15 mM $K_2HPO_4$. In some embodiments, the reaction buffer at final concentration comprises 10 mM $K_2HPO_4$ and has a pH of 7.4.

2. Denaturing Conditions

In some embodiments, the sample is exposed to denaturing conditions before hybridization of the probes. The denaturing conditions may be selected to denature all secondary structures in the target RNA or it may be selected to be partially denaturing and denature only certain secondary structures in the target RNA. In some circumstances, denaturing conditions comprise temperatures of from about 50 to 100° C. and/or chemical denaturants. Denaturing conditions as used above may include heating to a temperature ranging from 50-99° C., in some embodiments 70-99° C., in some embodiments 95-97° C., or 90° C.-95° C., depending on any detergent or chemical denaturant or salt present and probe composition (sequence, GC/AT content, length, and any modifications such as use of PNA). In the case of NaCl salt content of 10-100 mM and Tris-HCl or Tris-HCl-EDTA, pH 7.4, content of 10-150 mM, for example, heating to 95° C. for 15 seconds for a 50 µL reaction is sufficient to create denaturing conditions. A person of ordinary skill in the art is familiar with denaturing (including fully denaturing and partially denaturing) conditions.

3. Hybridization Conditions

In some embodiments, the hybridizing of the probe may occur at isothermal conditions and in other embodiments it may occur at thermocycling conditions. In some embodiments, hybridization of the probes occurs at a temperature of from 35 to 70° C.

If signal amplification is desired, thermocycling conditions may be used along with an excess of probe concentrations. In this manner, the probes bind to the target RNA, form a covalently bound fluorescent dye bridging the probes and then fall off the target RNA, new probes bind the target RNA, and so forth. Once the fluorescent dye bridging the probes has been formed as a covalent structure, it will remain structurally intact and will fluoresce under the correct conditions. This method allows for the generation of more fluorescent compounds as they fall off the RNA target and as new ones are formed.

It further being understood with respect to hybridization conditions that a probe annealing temperature range for the probes in Table 2, for example, would be 35-70° C., with a range, in some embodiments, of 40-60° C., with a reaction time at an isothermal annealing temperature of 10 sec to 1 hr, in some embodiments 15 sec to 2 min, in some embodiments 15 sec to 30 sec. With respect to both the isothermal and thermocycling embodiments, hybridization temperature and annealing temperature are essentially equivalent.

Optimal reaction temperatures for formation of the covalent bond between the non-reactive fluorogenic moieties on the ends of the probes in a probe set should allow both hybridization (annealing) between probes and target RNA template and the fluorescence-producing reaction, given a gap distance of 0-8 nucleotides between the probes hybridized to a target linear RNA sequence or a gap between the probes consisting of the RNA sequence within a nonlinear structure.

The covalent bonding between the probes sets upon binding to the target sequence, resulting in fluorescence, is likely essentially instantaneous. However, stabilization of the fluorescent emission is optimized by temperatures between 20° C. and 40° C.

The above example is considered to be an isothermal reaction. For thermocycling reaction conditions, the sample would be repeatedly heated to 95° C., then cooled to the annealing temperature of 40-60° C., followed by the reaction step at 20° C. to 40° C. However, the annealing temperature can be combined with the reaction step at a single temperature, for an exemplary thermocycling two-step procedure. In this case, the reaction temperature can match the annealing temperature or the reaction can be cooled slowly through the annealing temperature to reach the reaction temperature.

B. Employing Controls

The fluorogenic method may include positive and/or negative controls. For example, the method may further comprise normalizing the amount of fluorescence that is detected to the amount of fluorescence that is detected in a negative control sample that contains a non-target RNA sequence. The method may also further comprise normalizing the amount of fluorescence that is detected to the amount of fluorescence that is detected in a positive control sample that contains a target RNA sequence of known concentration.

Using one or more than one control can increase the accuracy of the quantification. For instance, the method may further comprise calculating the amount of each target RNA sequence in the test sample from the normalized amount of fluorescence detected.

C. Sample Description

In some embodiments, the test sample comprises mixed RNA species from cells. In some embodiments, the test sample is chosen from peripheral blood; lymph node; oral mucosa; gingival crevicular fluid (GCF); gut-associated lymphatic tissue (GALT); central nervous system (CNS) tissue, including brain tissue; cerebrospinal fluid (CSF); a mixed oral sample comprising oral mucosa, GCF, and saliva; and urine.

D. Methods of Treatment

The fluorogenic method may be combined with a method of treating the condition identified through the testing method. For instance, this may include a method of treating HIV, another pathogen infection (as described herein), cancer, etc., depending on the RNA target of the testing. Thus, methods of treatment further include administering a known medication to a patient identified as having the target RNA or methods may include assessing the effectiveness of candidate treatments.

A method of treatment may include the fluorogenic method described herein to test a sample from a patient and then further comprising administering an anti-HIV medication to a patient. A method of treatment may include performing the fluorogenic method on samples obtained from the patient (i) before, (ii) after, or (iii) before and after the medication was administered. In some instances, the anti-HIV medication is undergoing clinical trials. In some circumstances, the method is conducted to determine if the patient's HIV strain(s) are susceptible to the anti-HIV medication. It is also important clinically to identify patients with a latent HIV reservoir. Thus, a method can include obtaining a sample from the patient and administering an anti-HIV medication to the patient if the patient is found to have a latent HIV reservoir.

III. Test Kits

Test kits may be employed for quantitative detection of cell-associated HIV-1 RNA in a test sample comprising the any of the fluorogenic nucleic acid compositions described herein and at least one buffer. In some embodiments, the at least one buffer is a reaction buffer. A person of ordinary skill in the art may design appropriate reaction buffers. For example, the reaction buffer may comprise sodium chloride (NaCl) and potassium phosphate ($K_2HPO_4$). The reaction buffer at final concentration may comprise from 100 mM to 150 mM NaCl and from 5 mM to 15 mM $K_2HPO_4$. In some situations, the reaction buffer at final concentration comprises 10 mM $K_2HPO_4$ and has a pH of 7.4.

In some circumstances, the test kit comprises at least one pair of oligonucleotide probes to quantitatively detect spliced CD4+ RNA.

In some embodiments, the test kit comprises a positive control and/or a negative control. The negative control may comprise a non-target RNA sequence.

IV. Fluorogenic qLDR Compositions and their Use in Target Detection

Some nonlimiting embodiments of fluorogenic qLDR compositions and their use are provided in this section.

Chemically-engineered pairs of oligonucleotide or modified-backbone oligonucleotide probes are employed in qLDR technology to quantitatively detect the presence in a test sample of a target RNA sequence, such as a target RNA sequence containing an RNA spliced site or RNA secondary, tertiary, or quaternary structure, or linear RNA sequence containing neither a spliced site nor RNA secondary structure. Each pair of probes constitutes a "probe set" comprised of two probes: an upstream, first probe having a 5' and a 3' end; and a downstream, second probe having a 5' and a 3' end, which are complementary to upstream and downstream portions, respectively, of the target RNA sequence. To one end of each of the probes, a nonfluorescent reactive moiety comprising a portion of a fluorescent dye (fluorophore) is attached. The upstream and downstream portions of the target sequence may be selected with a gap of 0-8 nucleotides between them on a linear RNA or a gap consisting of the RNA sequence within a nonlinear structure. When and, in some embodiments only when, both of the probes in the probe hybridize to the target RNA sequence, the nonfluorescent reactive moieties on one end of each probe chemically react with each other. The nonfluorescent reactive moieties on the ends of each probe are designed to react with each other, across a distance of 0-8 nucleotides on a linear RNA or a distance consisting of the RNA sequence within a nonlinear structure, to form a covalent bond that creates a quantitatively-detectable fluorescent compound (a fluorophore). Of course, background fluorescence may occur due to random interactions between the probes in solution and such background fluorescence and binding of the two non-fluorogenic moieties to each other is within the scope of the disclosure.

Suitable gap distances may be estimated from basic principles of chemical structure as including a range of from about 2.5 to about 29.6 angstroms, approximately corresponding to 0-8 nucleotides between the nonfluorescent reactive moiety on the 5' or 3' end of the first probe sequence to the corresponding nonfluorescent reactive moiety on the 5' or 3' end of the second probe sequence, with a gap distance, in some embodiments, of from about 7.5 to about 18.5 angstroms, approximately corresponding to 3-5 nucleotides between the nonfluorescent reactive moiety on the 5' or 3' end of the first probe sequence to the corresponding nonfluorescent reactive moiety on the 5' or 3' end of the second probe sequence; it being understood that numeric assignment of gap distances in terms of angstrom units or number of nucleotides is provided as a general guideline illustrating such gap distances within ranges that are neither so small (steric hindrance) as to inhibit the nonfluorescent reactive moieties on an end of each of the probes in a probe set from reacting with each other when both probes in the probe set hybridize to the target RNA sequence, nor so large that the nonfluorescent reactive moieties on an end of each of the probes in a probe set are too far apart to efficiently interact with each other when both probes in the probe set hybridize to the target RNA sequence, but are not intended as parameters that require actual measurement. The adequacy of a gap distance for particular probe pairs in a particular probe set when hybridized to the upstream and downstream portions of a target RNA sequence may be ascertained situationally as needed by optimizing fluorescence output and reaction time. The use of covalently-bonded linkers between probe base sequences and nonfluorescent reactive moieties may also be employed and may allow targeting RNA sequences with no or a smaller gap than would be possible without the inclusion of linkers.

Probe set sequences are thus specifically selected in order to provide such a complementarity profile that detects the presence or absence of an RNA spliced site, or stem-loop or other secondary structure, or other linear RNA sequence, in some embodiments and not including background, when and only when both probes in the probe set hybridize to a target RNA sequence. When both probes in the probe set hybridize to a target RNA sequence, one end of each of the probes in the probe set (to which a nonfluorescent reactive moiety is attached) chemically reacts with the other, within the gap distance parameters as outlined above (0-8 nucleotides on a linear RNA or the RNA sequence within a nonlinear structure), to form a fluorescent compound whose fluorescence can be quantitatively detected.

The term "proximately abutting" as referring to the proximate distance between a first, upstream probe and a second, downstream probe in a probe set used in the fluorogenic compositions to detect a target RNA sequence may thus be understood as representing a gap distance of from about 2.5 to about 29.6 angstroms, approximately corresponding to 1-8 nucleotides between the nonfluorescent reactive moiety on the 5' or 3' end of the first probe sequence to the corresponding nonfluorescent reactive moiety on the 5' or 3' end of the second probe sequence, with a gap distance, in some embodiments, of from about 7.5 to about 18.5 angstroms, approximately corresponding to 3-5 nucleotides between the nonfluorescent reactive moiety on the 5' or 3' end of the first probe sequence to the corresponding nonfluorescent reactive moiety on the 5' or 3' end of the second probe sequence; it being understood that numeric assignment of gap distances in terms of angstrom units or number of nucleotides is provided as a general guideline illustrating such gap distances within ranges that are neither so small as to inhibit the nonfluorescent reactive moieties on an end of each of the probes in a probe set from reacting with each other when both probes in the probe set hybridize to the target RNA sequence, nor so large that the nonfluorescent reactive moieties on an end of each of the probes in a probe set are too far apart to interact with each other when both probes in the probe set hybridize to the target RNA sequence. Gap distances are not, however, intended as parameters that require actual measurement. Further as noted above, the adequacy of a gap distance for particular probe pairs in a particular probe set hybridizing to a given target RNA sequence may be ascertained situationally by optimizing fluorescence output and reaction time.

To summarize, each probe set is engineered to include nonfluorescent reactive moieties that react to create a fluorophore, in some embodiments and not including background, when and only when the two probes undergo an RNA-templated reaction of the nonfluorescent reactive moieties after hybridizing of both probes in the probe set to their respective upstream and downstream portions of the target RNA sequence, with a gap of 0-8 nucleotides between the probes on a linear RNA or a gap consisting of the RNA sequence within a nonlinear structure.

The nonfluorescent reactive moieties on the ends of each probe are thus designed to react with each other, separated by 0-8 nucleotides on a linear RNA or separated by the RNA sequence within a nonlinear structure, to form a covalent bond that creates the quantitatively-detectable fluorescent compound. However, the probe ends in a given probe set are not in close proximity and do not react in a significant amount (other than a low level of background) to form a fluorescent dye unless specifically templated by a target RNA sequence such as a spliced site, RNA secondary structure, or linear RNA sequence, with a gap distance of 0-8 nucleotides between the two probes on a linear RNA or a gap consisting of the RNA sequence within a nonlinear structure.

Accordingly, the target sequence is complementary to the two probes in the probe set, but the probes react together to form a covalent bond that creates a quantitatively detectable fluorophore, in some embodiments and not including background, when and only when both probes in the probe set hybridize to their respective upstream and downstream portions of the target sequence, with a gap distance of 0-8 nucleotides between the two probes on a linear RNA or a gap consisting of the RNA sequence within a nonlinear structure. The fluorogenic ends of the probes in the probe set are permissive for the fluorogenic reaction to occur, only as a function of hybridization of both probes to the target sequence. Such a templated reaction, in some embodiments and not including background, when and only when it occurs, produces a stable, quantitatively detectable, real-time, fluorescent readout for highly-precise and accurate determinations, for example, of exact sequence and degenerate splice sites in single-stranded RNA or stem-loops or other topological configurations within secondary structure RNA.

Thus, embodiments include the making and using of chemical compositions for qLDR-based, quantitative detection of target ribonucleic acid sequences including RNA spliced sites, RNA stem-loops or other RNA secondary, tertiary, or quaternary structures, or RNA linear sequences. Such embodiments include chemical compositions comprising probe sets engineered to fluoresce in some embodiments and not including background, when and only when templated by hybridizing to such a target sequence and having a gap between the hybridized reactive probe ends of 0-8 nucleotides on a linear RNA or a gap consisting of the RNA sequence within a nonlinear structure. Methods and assays that deploy such probe sets, as well as kits for effectuating their deployment by end users, are also provided for a broad range of research and clinical applications.

V. Chemical Compositions—Fluorogenic Probe Sets

Certain nonlimiting embodiments of chemical compositions for fluorogenic probe sets are provided in this section.

Chemical compositions include, fluorogenic nucleic acid probes chemically engineered to provide quantitative detection of target RNA sequences. Alternative embodiments include target RNA sequences that contain an RNA spliced site resulting from a splicing event; target RNA sequences that contain a stem-loop resulting from RNA secondary structure, such as an RNA pseudoknot; and target RNA sequences that contain neither a spliced site nor a stem-loop. Certain fluorogenic compositions may thus broadly be characterized as follows:

A. Fluorogenic Composition (1):

A fluorogenic nucleic acid composition for quantitative detection of a target RNA sequence in a test sample, comprising:

(a) at least one pair of oligonucleotide or modified-backbone oligonucleotide probes comprising an upstream, first probe having a 5' end and a 3' end, and a downstream, second probe having a 5' end and a 3' end, forming a probe set of two probes;

(b) wherein the first probe and the second probe are complementary to an upstream and a downstream portion, respectively, of the target RNA sequence, and further wherein the upstream and downstream portions of the target RNA sequence to which the probes bind have a gap of 0-8 nucleotides on a linear RNA or a gap consisting of the RNA sequence within a nonlinear structure. A chemical reaction to form fluorescent moiety, in some embodiments and not including background, when and only when both probes of the probe set hybridize to the target nucleic acid sequence; and (c) wherein one end of each of the first probe and the second probe is chemically attached to a nonfluorescent, reactive moiety, such that the nonfluorescent, reactive moieties on the probe-abutting ends of each of the two probes in the probe set are capable of reacting to form a covalent bond that produces a fluorescent compound whose fluorescence emissions are quantitatively detectable in some embodiments and not including background, when and only when both probes of the probe set hybridize to the target RNA sequence and the ends of the probes containing the fluorescent moieties are separated by 0-8 nucleotides on a linear RNA or a gap consisting of the RNA sequence within a nonlinear structure.

VI. Specific Applications of qLDR Compositions and Methods

Some nonlimiting embodiments describing specific applications are described herein.

The fluorogenic nucleic acid compositions described above may be used in qLDR technology to quantitatively detect target nucleic acid sequences by employing compositions, reagents, methods, assays, and kits for detecting the fluorescence emitted by the fluorogenic nucleic acid probes in a probe set when they react to form a fluorescent compound upon hybridizing to a target sequence.

For purposes of describing the compositions, reagents, methods, assays, and kits, "a fluorescent-probe detection set" conveniently may be defined as Fluorogenic Composition (1).

More specifically, methods may broadly be characterized as comprising Fluorogenic Method (1):

(1) A fluorogenic method for quantitative detection of a target ribonucleic acid (RNA) sequence in a test sample, comprising the steps of:

(a) adding to each RNA test solution a fluorescent-probe detection set for each target RNA sequence, in sufficient quantity to form an RNA detection solution comprising a uniform fluorescent-probe detection set final concentration from 1 pM to 1 μM in each RNA detection solution, in some embodiments from 1 pM to 100 nM, in some embodiments from 100 nM to 1 μM, in some embodiments from 1 fM to 1 μM; in some embodiments from 1 pM to 500 pM.

(b) exposing each RNA detection solution to denaturing conditions;

(c) hybridizing the fluorescent-probe detection set for the target RNA sequence in each RNA detection solution at a temperature in the range of 35° C. to 70° C. (in some embodiments 40° C. to 60° C.), under isothermal or thermocycling conditions;

(d) detecting with a detector the amount of fluorescence emitted by the fluorescent compound formed when the fluorescent-probe detection set hybridizes to the target RNA sequence in each RNA detection solution;

(e) optionally normalizing the amount of fluorescence that is detected in each RNA detection solution to the amount of fluorescence that is detected in a parallel control sample that contains a non-target RNA sequence as a negative control; and (f) optionally normalizing the amount of fluorescence that is detected in each RNA detection solution to the amount of fluorescence that is detected in a parallel control sample that contains a known concentration of the target RNA sequence as a positive control; and (g) optionally calculating the amount of each target RNA sequence in the test sample from the normalized amount of fluorescence detected from each RNA detection solution.

Additionally, it is further pointed out that practice of the above fluorogenic method (I) may also include one or more of the following additional steps of:

optionally lysing the cells by osmotic shock, sonication, microwave, chemical, freeze-thaw or mechanical disruption treatment, prior to the addition of probes;

optionally treating the lysed cells with DNase I and protease prior to the addition of fluorogenic probes, to remove genomic DNA and proteins that may be bound to the RNA targets or inhibit the reaction.

optionally purifying RNA from the lysed cells via column method, precipitation or other purification method prior to the addition of probes;

optionally amplifying the RNA from the lysed cells using random or specific primers or oligo-dT primer or degenerate primers, prior to the addition of probes;

optionally calibrating the RNA level detected to the number of starting cells via cell count or PCR or ddPCR or qPCR or RT-qPCR of DNA or RNA endogenous or exogenous or encapsulated, spiked in or not spiked in, multiplexed or side-by-side; and optionally, helper oligos (accessory primers), complementary to a region that immediately flanks a target RNA sequence, may be added to a reaction to optimize the fluorogenic reaction or mitigate the effects of RNA secondary or higher order (tertiary or quaternary) structures on target accessibility to the fluorogenic probes.

VII. Use of qLDR Technology to Provide a Reference Standard

The present methods and compositions, in some nonlimiting embodiments, may be used to provide a reference standard.

The fluorogenic compositions and methods may be employed to provide a quantitative reference standard for calibrating levels of particular target RNA sequences, which represents an acute need, especially for example, in monitoring cell-based HIV-1 RNA levels in HAART patients, for which no such quantitative RNA standard exists in the prior art. This may be accomplished using fluorogenic method (I), for example, to calibrate RT-qPCR, RT-ddPCR, RT-LAMP or other RNA detection assay, because the fluorogenic method is unique in detecting RNA directly, without the need for a DNA intermediary, or for nucleic acid amplification.

VIII. Use of qLDR Technology in Quantitative Detection of HIV Levels

In some embodiments, the qLDR technology may be used to quantify detection of HIV levels; however, the described embodiments are nonlimiting.

Specific application of qLDR technology to quantitative detection of HIV levels in latent and activated reservoirs is provided below as exemplary of the compositions, reagents, methods, assays, and kits.

A. Multiplex Detection of Cell-Based HIV-1 RNA by qLDR

A schematic diagram of a process for multiplex detection of cell-based HIV-1 RNA from samples (for example, CD4+-enriched PBMC from peripheral blood or mixed gingival crevicular fluid (GCF) and oral mucosa) to quantitation of total cell-based HIV-1 RNA is provided in FIG. 1.

Resting CD4+ cells may be isolated from the peripheral blood mononuclear cell (PBMC) fraction of patient blood samples. These cells may be cultured and activated or untouched prior to qLDR testing. Latent and resting T cell lines may be activated using PMA and ionomycin or PHA or any other activator of T cells or latent HIV genomes for qLDR testing with probe sets over a time course of 0-14 days. Total cellular mRNA may be extracted or released from cell line samples consisting of $1-5 \times 10^6$ cells from each sample of a dilution series prepared from total or crude cell RNA in buffer and tested for purity and concentration. RNA may be extracted or released directly from oral mucosa and GCF samples, as a much lower number of cells, with higher activation level, compared to blood will be present. qLDR may be performed on the three types of samples, individually or in combination, as well as in comparative testing with RT-qPCR.

Quantitative detection of target RNA sequences may thus be performed on a broad range of test samples, including peripheral blood, lymph node, oral mucosa, gingival crevicular fluid (GCF), and saliva, as well as a mixed oral sample comprising oral mucosa, GCF, and saliva. Suitable test samples further include CD4+ enriched peripheral blood mononuclear cells (PBMC), lymph nodes containing B cell follicles, gut-associated lymphatic tissue (GALT), central nervous system (CNS) tissue, including brain tissue, cerebrospinal fluid (CSF), seminal fluid, ocular fluid, sebaceous fluid, and urine.

B. HIV-1 Spliced Site Targets for Optimized qLDR Probes

For quantitative detection of HIV-1 in RNA from patient blood, oral mucosa, or GCF, a probe length of between 5 and 40 bases complementary to HIV-1 RNA may be used. In some embodiments, a probe between 5 and 30 bases may be used. As indicated above, shorter sequences may be used. HIV-1 target sequence regions suitable for HIV-1 qLDR probes are provided in Table 2 and include rearrangements of these sequences and any resulting junctions that occur through mutation, splicing or selection from natural or artificial events.

1. HIV-1 Spliced Sites Amenable to qLDR Detection

HIV-1 RNA is spliced into different sizes as part of the protein expression process in HIV. The 9 kb of HIV RNA is spliced into 2 kb, 4 kb, and 1 kb pieces. Cells actively infected by HIV generally comprise all the spliced forms. Cells with a latent infection may not have all the spliced forms, but generally have the 2 kb splice form.

HIV-1 spliced sites amenable to qLDR detection include:

(A) Cell-based 2 kb RNAs are spliced at donor site 1 (D1) variably to acceptor sites A3, A4(a,b,c), or A5, but all uniquely contain D4-A7 splicing, are expressed early in HIV-1 replication, and are retained in the nucleus of latent CD4+ T cells until activation.

(B) Early activation results in 4 kb RNAs with similar variable D1-A3,4,5 splicing but all lack D4-A7 and thus contain an intact sequence 3' of the D4 site and 5' of the A7 site and contain the intronic region between D4 and A7 splice sites.

(C) In late activation, the 9 kb full-length HIV-1 genome is produced, which uniquely contains an intact sequence 3' of the D1 spliced site, the intronic region between D1 and any A acceptor site, as well as the same intact D4 and A7 spliced sites as the 4 kb RNAs.

Optimization of the length and composition of probes complementary to HIV-1 spliced and unspliced sequences to maximize the efficiency of qLDR may be achieved by comparison of probes designed based on the differences described above for 2 kB, 4 kB, and 9 kB HIV-1 RNA sequences. The Tat (transactivator) and Rev proteins are encoded by the cell-based 2 kb HIV-1 spliced RNAs, through the D4-A7 spliced site. Tat binds to TAR to allow high processivity of host RNA polymerase primary transcript production. In early activation of latent cells, the 2 kb RNAs exit the nucleus, and expressed Rev protein facilitates transport of HIV-1 RNA species into the cytoplasm for translation and virus particle assembly. The alternatively spliced Tat and Rev mRNA and the Tat and Rev proteins are produced at a low level in latent HIV-1 infected cells. Thus, detection of spliced Tat/Rev mRNA facilitates accurate quantification of the latent pool, due both to its low copy number and because its advanced location on the primary transcript is indicative of transcriptional competence in HIV-1 latent cells.

The Tat/Rev D4-A7 spliced site (spanning nucleotides 6045-8379) is conserved across HIV-1 subtypes. The D4 and A7 unspliced sites are retained in the cell-based 4 kb spliced HIV-1 RNAs, to allow for expression of the viral envelope protein. The cell-based 4 kb RNAs are expressed at a higher level in the intermediate time point of activation. These unspliced sites are also present in the cell-based 9 kb full-length transcript expressed at late stages of virus replication from activated latent cells. The D1 unspliced site or the intronic region after the D1 splice site is specific to the cell-based 9 kb full-length transcript, expected to be present at high levels only during later activation time points and in viral particles released into the plasma, GCF, or extracellular within the oral mucosa. Subtraction of the amount of measured cell-based (i.e., not including detection of released viral particle RNAs) D1 unspliced site from the amount of measured D4 or A7 unspliced sites will yield the amount solely of the cell-based 4 kb HIV-1 RNAs.

As applied to optimizing quantitation of HIV-1 RNA, qLDR can differentially quantify all three HIV-1 RNA size groups expressed at each stage: Measuring the level of the D4-A7 spliced site with unique probes and qLDR will only yield the level of 2 kb HIV-1 RNAs, which are expressed in latent cells but retained in the nucleus until activation. Measuring the level of either the D4 or the A7 unspliced site, or intron region between the D4 and A7 splice sites, will quantify all of the 4 kb RNAs (expressing the Env protein) and the 9 kb RNA (full-length HIV-1 genome, expressing the Gag-Pol as well as the Env proteins). Measuring the level of the D1 unspliced site or intron will quantify only the 9 kb full-length HIV-1 genome. Subtracting (3) from (2) will yield the level of only the 4 kb RNAs.

In vitro transcribed HIV-1 RNA templates for kit assay controls may be synthesized to include: (A) an HIV-1 sequence of 2,105 nt containing the D1-A5 and D4-A7 spliced sites and with the TAR hairpin region removed to allow for efficient in vitro transcription using the T7 promoter in a pET vector; (B) an HIV-1 sequence containing both the D1 and D4 unspliced sites or intronic regions, with the size chosen to be easily distinguished on a gel from the (A) sequence size; and (C) an HIV-1 sequence containing only the D4 unspliced site or intronic regions, again with a unique size. These three RNA transcripts permit in vitro testing and optimization of the ability to accurately quantify and differentiate between the levels of transcripts containing each of the spliced or unspliced sites.

Sensitivity: quantitative viral outgrowth assay (Q-VOA), the current standard for quantification of the peripheral blood HIV-1 latent reservoir, yields a detection level of 1 latent HIV-infected CD4+ T cell in a million ($10^6$) resting CD4+ T cells from PBMC, after 2-3 weeks and several types of activation. The Q-VOA assay modified for a shorter activation period of 2-7 days and with RT-qPCR detection of both cell-based and released viral HIV-1 RNAs, yields a detection level of up to 15 CD4+ T cells/$10^6$ resting CD4+ T cells. It is expected that the actual size of the peripheral blood latent reservoir lies in the region of 20-30, and possibly up to 60, cells per $10^6$ resting CD4+ T cells. There are no such quantitative numbers available in the prior art for the HIV-1 latent reservoir in the oral environment, including the oral mucosa and GCF.

Quantitative measurements for the HIV-1 latent reservoir can, however, be obtained using the fluorogenic compositions and methods. Test kits for quantitative detection of cell-associated HIV-1 RNA in a test sample may also be fashioned to include, for example, (a) a fluorescent-probe detection set to detect 2 kb spliced HIV-1 RNA; (b) a fluorescent-probe detection set to detect 4 kb spliced and 9 kb full-length HIV-1 RNA; (c) a fluorescent-probe detection set to detect 9 kb full-length HIV-1 RNA; and (d) a concentrated reaction buffer comprising, after final dilution, a concentration of NaCl in the range of 100 mM to 150 mM and 10 mM potassium phosphate ($K_2HPO_4$) buffer at pH=7.4. Alternatively, a concentrated reaction buffer comprising, after final dilution, 10 mM Tris-HCl and 1 mM EDTA, at a pH in the range of 7.0 to 8.0, in some embodiments 7.5, may also be used.

A control probe set for spliced CD4 RNA may also be included with a test kit as described above, or included as a separate, control kit. Such a separate control kit may contain (1) a fluorescent-probe detection set to detect spliced CD4 RNA; and (2) a reference target sequence comprising each of the HIV-1 target RNA sequences in (a) through (c) of the test kit. In some embodiments, such a separate control kit also includes (3) a control reference material comprising a control fluorogenic probe set and corresponding non-target RNA sequence. The separate control kit, like the test kit, also contains a concentrated reaction buffer as described for the test kit. The control reference material may additionally be used as a spike-in internal control. The separate control kit may also contain one or more fluorogenic probe sets to detect one or more housekeeping RNAs, along with corresponding target RNA sequences as positive controls.

EXAMPLES

Example 1

HIV-1 qLDR Probe Working Concentration Ranges

Probe sets for use in qLDR assay of HIV-1 were prepared using sequences as listed in Table 2, with SEQ ID NOS: 9 and 10 in PNA form as described in the footnote of Table 2. DNase- and RNase-free water, potassium phosphate, and sodium chloride were purchased from Sigma-Aldrich or Fisher Scientific. PNA probes were purchased from PNABio and were HPLC purified and verified by MS-MALDI; DNA oligonucleotide probes were purchased from Gene Link and were HPLC purified. Cy3 and Cy5 fluorogenic dye halves were synthesized at Cornell University in the Department of Bioengineering or purchased through Sigma Aldrich. HIV-1 and random RNA (CD4 mRNA) templates were produced by reverse transcription from T7 plasmids (GenScript) amplified in *Escherichia coli* and verified by DNA sequencing at the Cornell Biotechnology Resource Center (BRC). RNA lengths were verified by agarose gel electrophoresis and concentrations were determined by NanoDrop™ ND-1000 spectrophotometer (NanoDrop Technologies, Inc.).

Stock solutions of each probe set and HIV-1 or random RNA template at the specified concentrations were prepared in water and serially diluted as needed. For each experiment, 20 μL of potassium phosphate ($K_2HPO_4$) buffer (25 mM, pH=7.4, containing 375 mM NaCl) and 10 μL of each stock solution were transferred into each well to make the final concentrations of 10 mM potassium phosphate and 150 mM NaCl. Reactions were performed in a 96-well plate using a Fluoroskan II 373 fluorescence plate reader (Thermo Labsystems). Reactions were carried out at the temperatures specified (25° C., 37° C., or thermocycled) and detected with $\lambda_{550\ nm}$ excitation and $\lambda_{584\ nm}$ emission filters.

Figure 5:
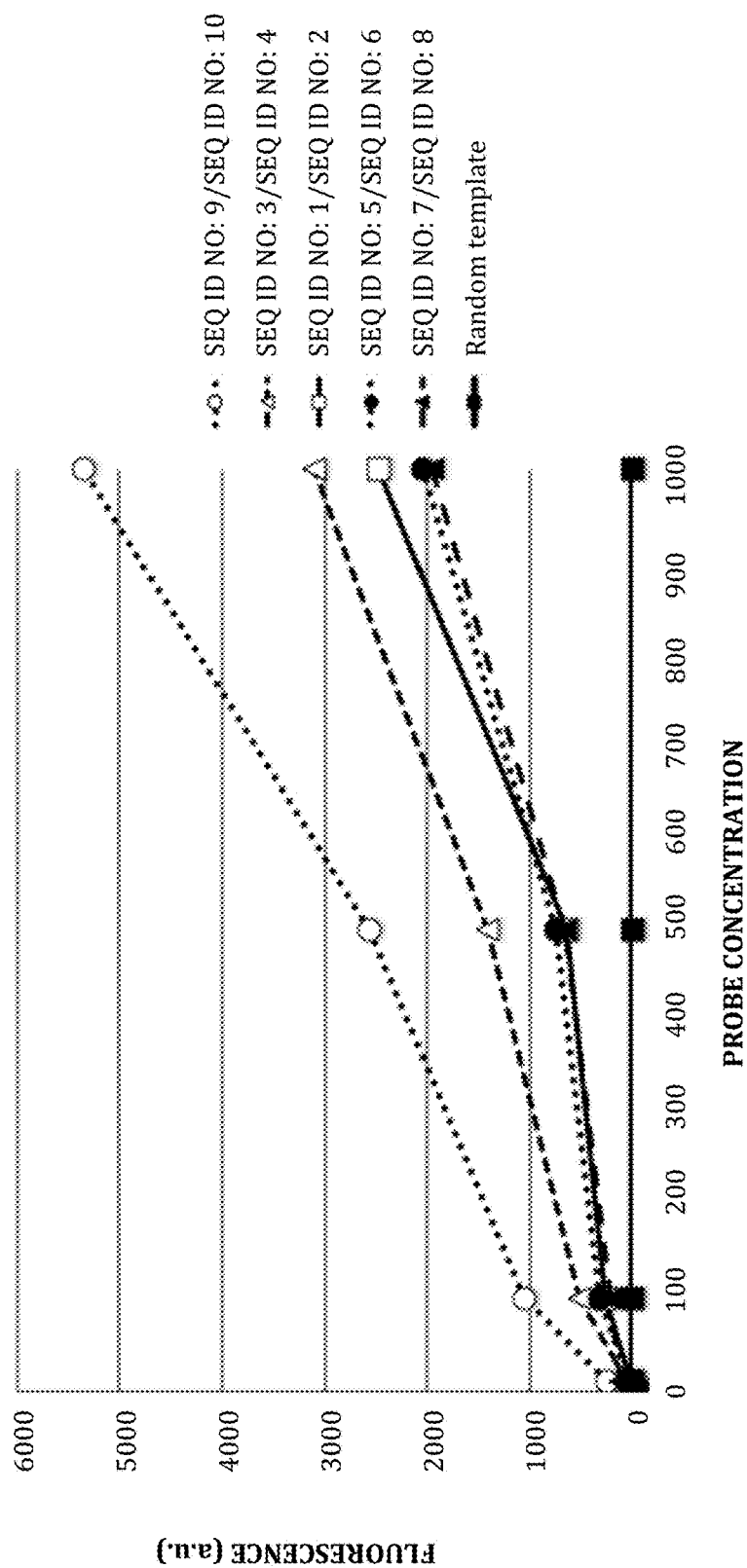
FIG. 5 provides HIV-1 qLDR probe working concentration ranges. Fluorescence measurements taken over a range of probe concentrations from 0 pM to 1M, using the probes specified in FIG. 5 and the corresponding target RNAs specified in Table 2. A random template control was tested with each probe set and consisted of an off-target RNA for each probe set. Data for a representative random template control are shown. Probe sets referred to in FIG. 5 correspond to the probes indicated in Table 2 with respective nucleic acid sequences, HIV-1 gene origins, genome locations, and target regions. Materials and methods used are provided in Example 1.

Working concentration ranges prepared for the HIV-1 probes listed in Table 2 above were measured. Results for the probes tested are shown in FIG. 5.

Example 2

HIV-1 qLDR Sensitivity

Figure 6:
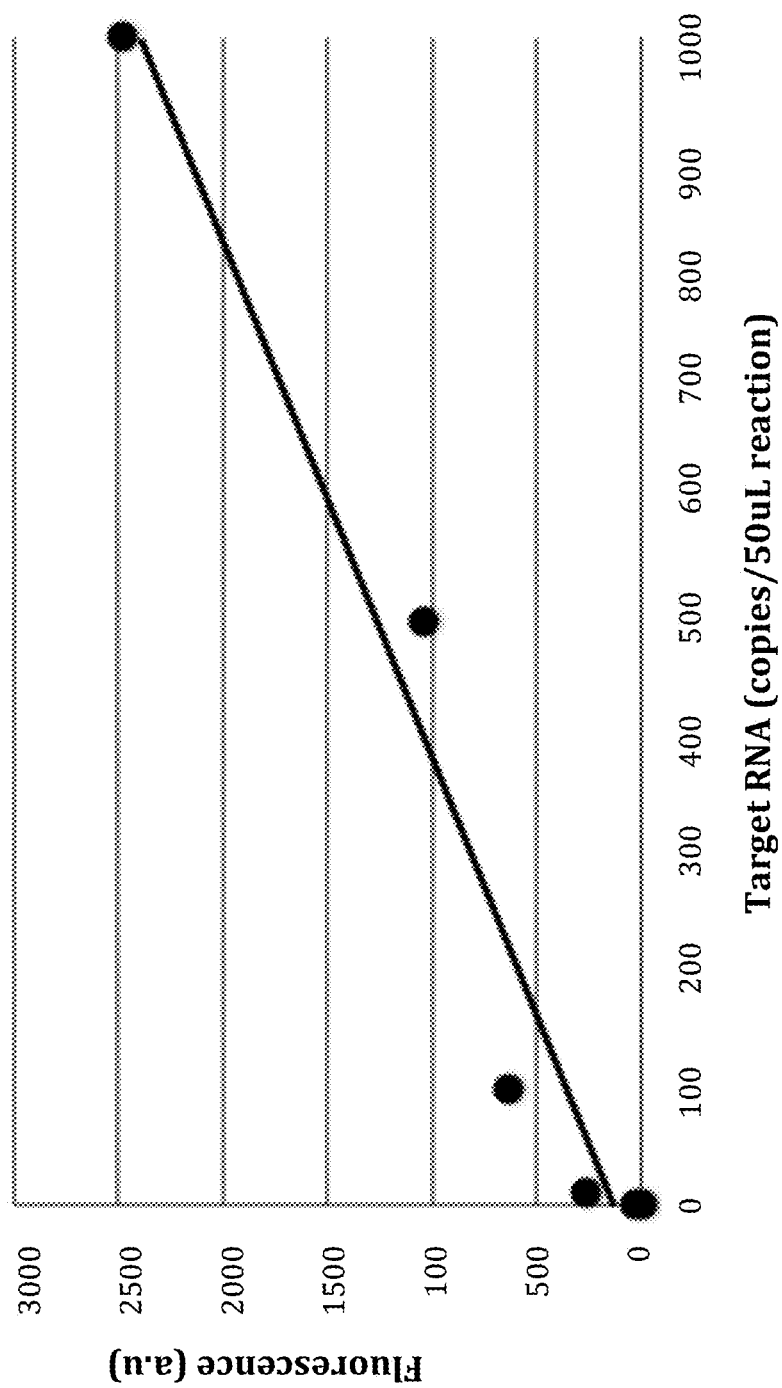
FIG. 6 illustrates HIV qLDR fluorescence yield to template concentration (Sensitivity of HIV qLDR). Data for probe set SEQ ID NO: 1/SEQ ID NO: 2 are shown as an example with its corresponding HIV RNA target as specified in Table 2. Materials and methods used are provided in Example 2.

Sensitivity of HIV qLDR was measured by comparing HIV qLDR fluorescence yield to template concentration. Time of reaction was 15 min at 25° C. with probe set SEQ ID NO: 1/SEQ ID NO: 2. The HIV-1 RNA template concentration range was 0-1000 copies/50 μL reaction; salt concentration was 150 mM NaCl; pH 7.4 in 10 mM potassium phosphate buffer. Fluorescence was measured in a 96-well plate in a Fluoroskan II 373 with $\lambda_{550\ nm}$ excitation and $\lambda_{584\ nm}$ emission filters. Results are shown in FIG. 6.

Example 3

Isothermal and Thermocycling qLDR Detection

Figure 7:
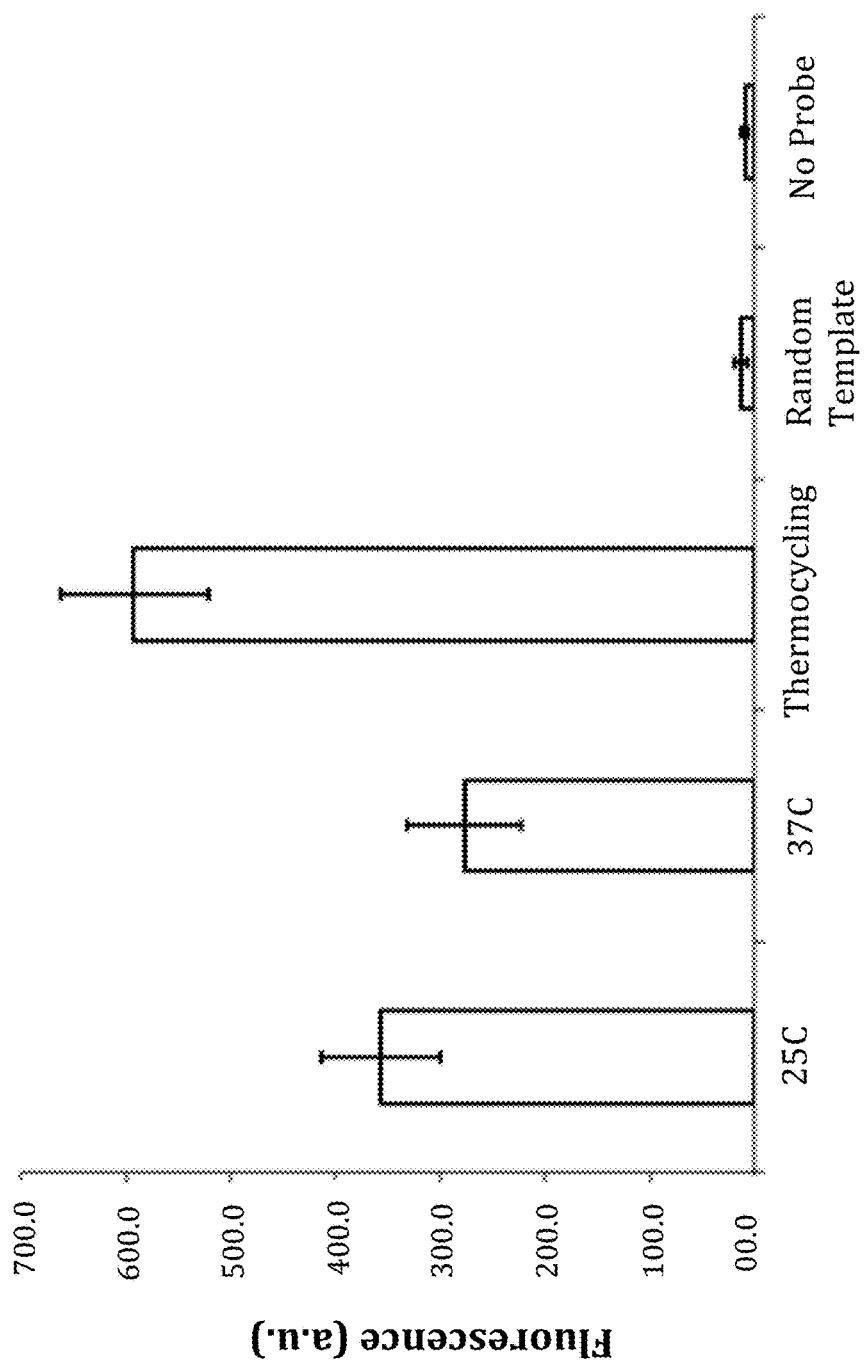
FIG. 7 shows effect of temperature on HIV qLDR fluorescence yield. Data for probe set SEQ ID NO: 1/SEQ ID NO: 2 are shown as an example with its corresponding HIV RNA target as specified in Table 2. Materials and methods used are provided in Example 3.

The effect of temperature on HIV qLDR fluorescence yield was studied. Times of reaction were 15 min for 25° C. and 30 min for 37° C. Thermocycling was performed for 10 cycles of 95° C. for 15 s, 55° C. for 15 s, 25° C. for 30 sec, followed by fluorescence measurement at 25° C. No template and no probe controls were performed at 25° C. for 15 min Fluorescence was measured at the times specified in a 96-well plate in a Fluoroskan II 373 with $\lambda_{550\ nm}$ excitation and $\lambda_{584\ nm}$ emission filters. The probe set used was SEQ ID NO: 1/SEQ ID NO: 2; HIV-1 RNA template concentration was 10 copies/50 µL reaction; salt concentration was 150 mM NaCl; pH 7.4 in 10 mM potassium phosphate buffer. Results are shown in FIG. 7.

Example 4

HIV qLDR Quantification of Cell Number

Figure 8:
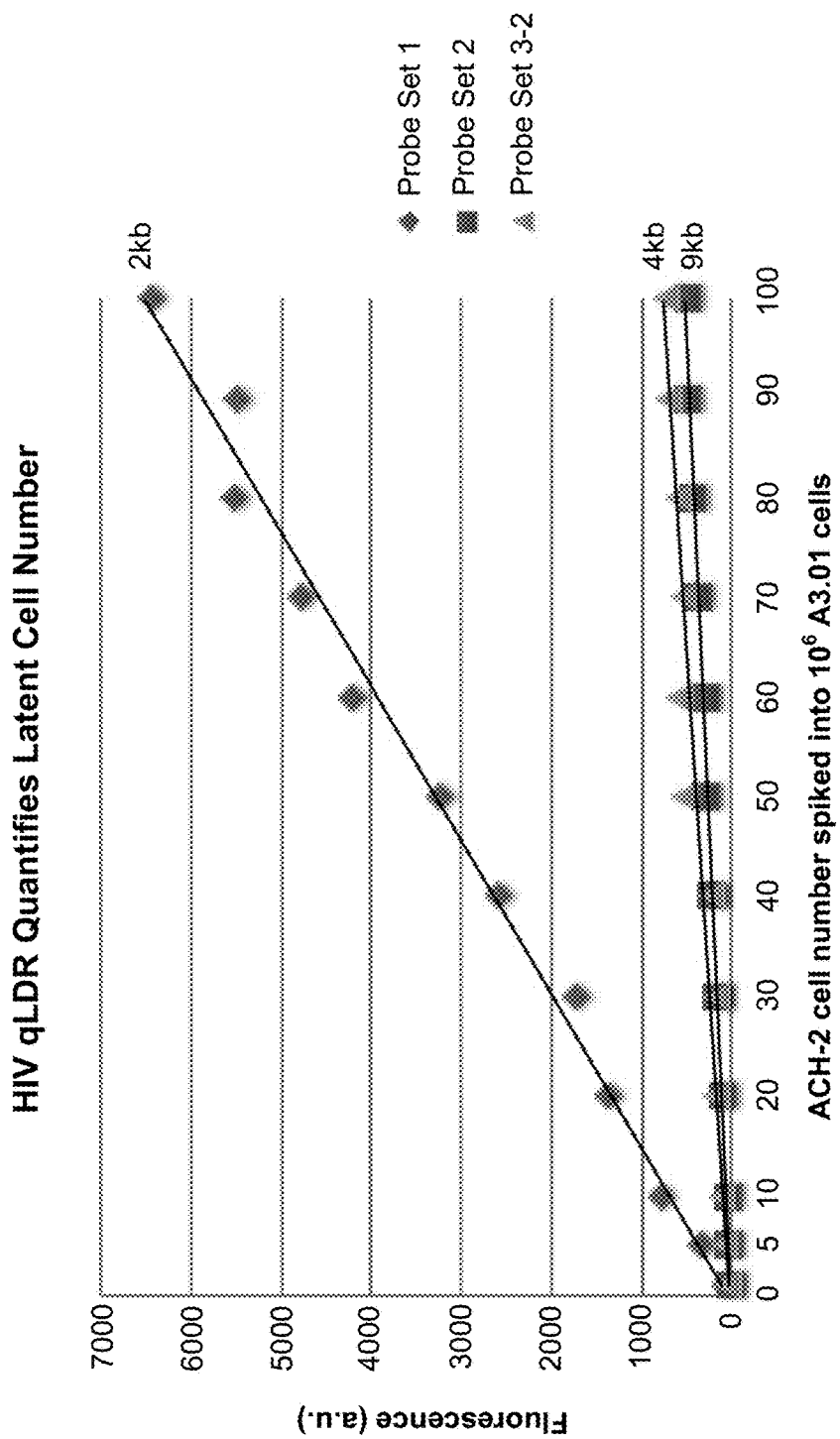
FIG. 8 demonstrates that HIV qLDR yields fluorescence tightly correlated to cell number.

With calibration, HIV qLDR yields fluorescence tightly correlated to cell number (FIG. 8). The qLDR probe sets were tested against HIV latent cell line ACH-2 and its parent uninfected cell line A3.01. Cells were cultured in T-75 flasks in RPMI 1640 medium, 10 mM HEPES, 2 mM L-glutamine, 90%, with 10% FBS, grown to 80% confluency (approximately $6 \times 10^6$ cells per T-75 flask) and harvested by cell scraper. Cells were counted and a dilution series was set up for 0, 1, 5, 10, 20, 30, 40, 50, 60, 70, 80, 90, and 100 ACH-2 cells per $10^6$ A3.01 cells. Cells were washed with 1×PBS, concentrated and resuspended in 1×PBS and lysed using proteinase K lysis, followed by DNase I treatment. No final heat inactivation step was required and RNA extraction was not needed.

The qLDR reaction contained optimized probe concentrations at 10-100 pM and a total reaction volume of 50 µL. The qLDR reaction for each probe set was optimized against the commensurate synthetic HIV RNA targets using fluorescence microscopy and fluorescence emission in a 96-well format in a desktop fluorometer, with readings normalized to background. FIG. 8 shows the tight correlation of fluorescence level to latent ACH-2 cell number observed in $10^6$ cells of the uninfected parent A3.01 cell line. In the nonactivated latently infected ACH-2 cells, multiply-spliced 2 kb HIV RNA, using qLDR with probes SEQ ID NO: 9/SEQ ID NO: 10) proved most useful for cell number determination, while levels of 9 kb transcripts (SEQ ID NO: 1/SEQ ID NO: 2) and 4 kb transcripts (fluorescence from qLDR using probes SEQ ID NO: 1/SEQ ID NO: 2 subtracted from fluorescence using probes SEQ ID NO: 5/SEQ ID NO: 6) were clearly far less prevalent, despite comparable detection efficiency as determined by initial testing with synthetic HIV RNA targets.

Example 5

HIV qLDR Differentiates Latent Vs. Active HIV-Infected Human Cells

Figure 9:
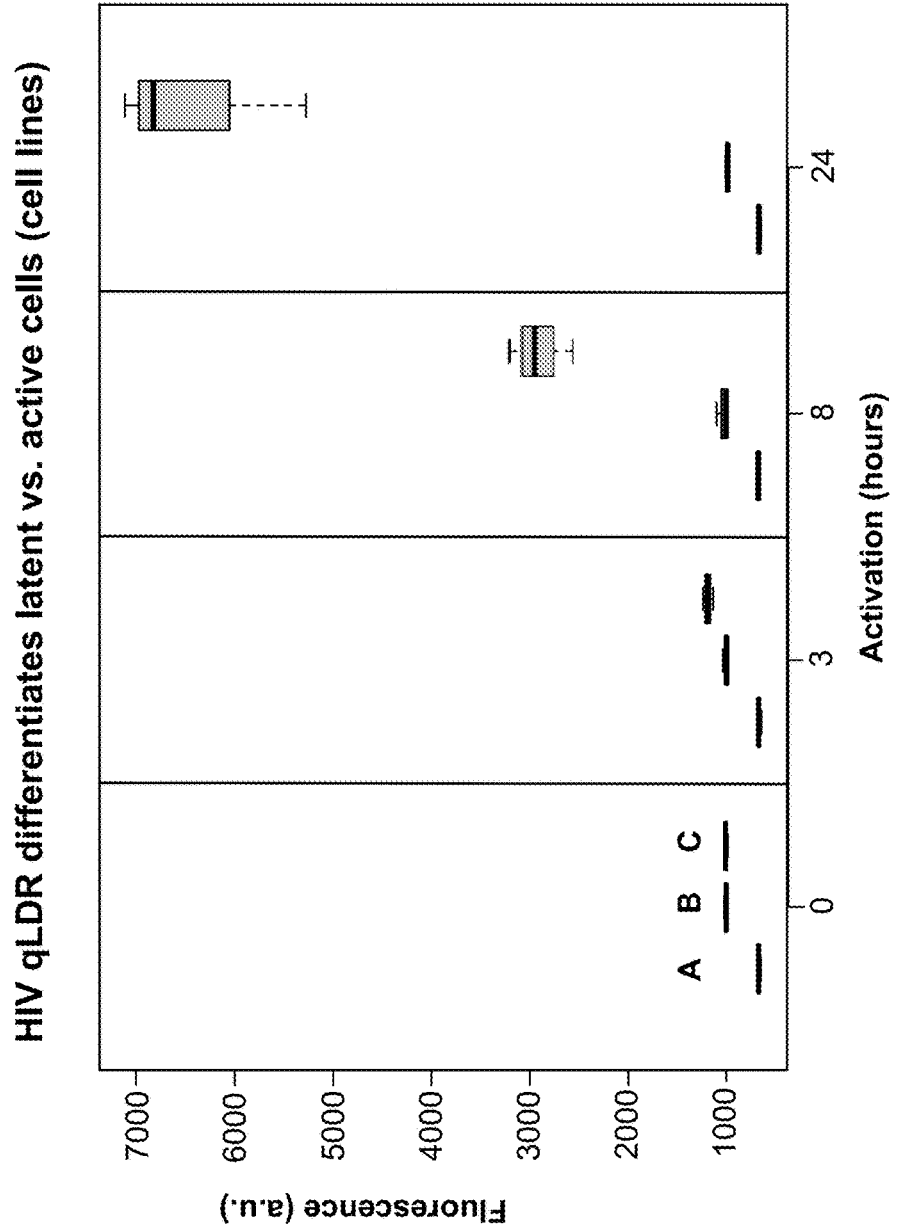
FIG. 9 shows that HIV qLDR can differentiate between latent and active HIV-infected cells in experiments using cell lines.
Figures 10A, 10B:
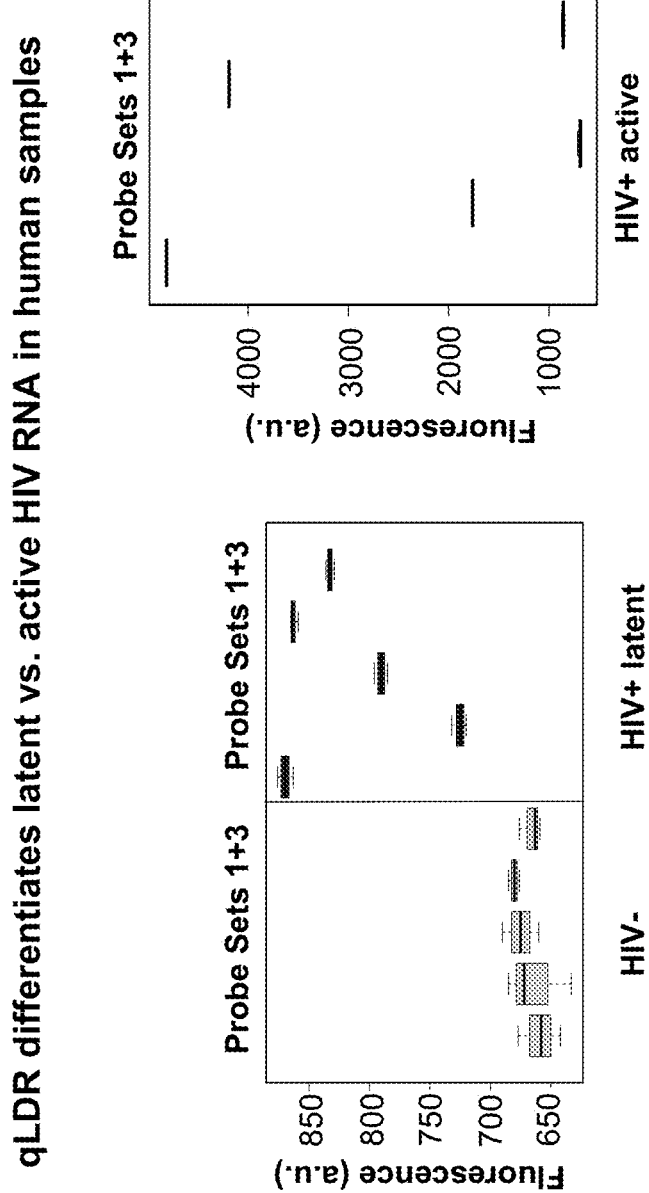
FIGS. 10*a-b* show that HIV qLDR can differentiate between latent and active HIV-infected cells in human CD4+ T cells isolated from peripheral blood.
Figure 11:
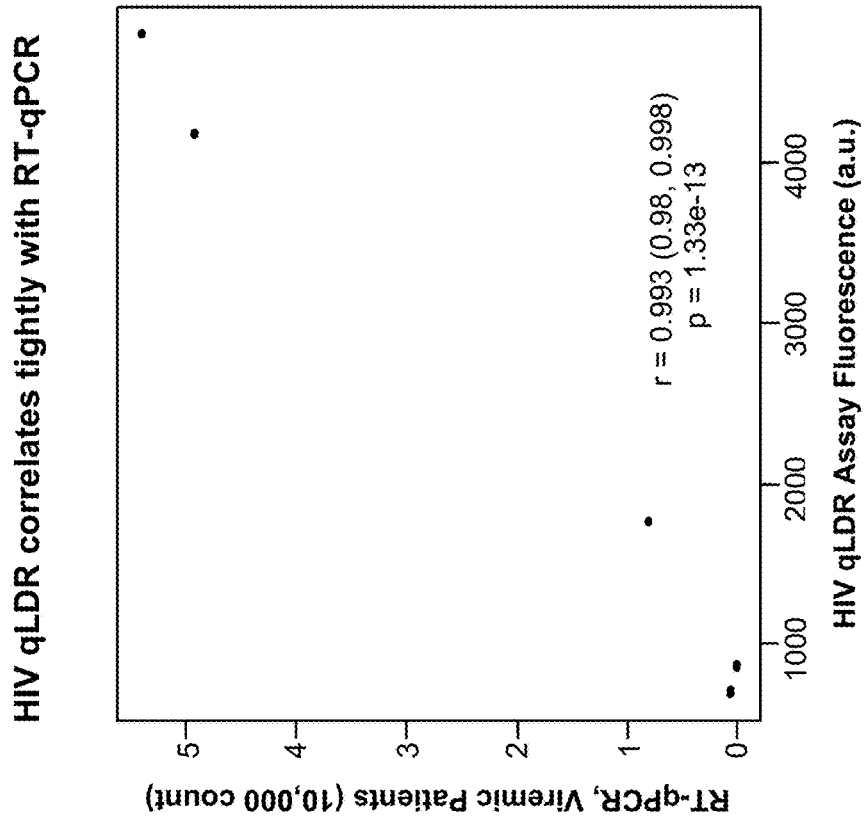
FIG. 11 shows that HIV qLDR results closely correlate with HIV RT-PCR results for the same human CD4+ T cells isolated from peripheral blood.

HIV qLDR can differentiate between latent and active HIV-infected cells, both in experiments using cell lines (FIG. 9) and in human CD4+ T cells isolated from peripheral blood (FIG. 10a-b). HIV qLDR results closely correlate with HIV RT-PCR results for the same human CD4+ T cells isolated from peripheral blood (FIG. 11).

For cell line testing (FIG. 9), ACH-2 and A3.01 cells were grown in T-75 flasks and plated at 1 mL per well in a 24-well culture plate in RPMI medium. After the wells reached 60% confluency, cells were activated for 0, 3, 8, and 24 hr with PMA (phorbal 12-myristate 13-acetate) at 1 µM final concentration per well. The experiment was performed such that each activation time endpoint represented the same total growth time. The activated ACH-2 cells were harvested from each well and counted. After preservation and shipping in 90% FBS/10% DMSO at −80° C., the cell suspensions were recounted, diluted and added at 10 cells into $10^6$ A3.01 cells activated for the matching time period. HIV qLDR, using probes SEQ ID NO: 9/SEQ ID NO: 10 for 2 kb tat-rev transcripts, SEQ ID NO: 1/SEQ ID NO: 2 for 9 kb transcripts, and SEQ ID NO: 1/SEQ ID NO: 2 and SEQ ID NO: 5/SEQ ID NO: 6 for 4 kb transcripts, was performed on the cells and fluorometric readings in a 96-well plate format were normalized to background. The HIV qLDR probe sets differentiated between latent and active ACH-2 cells, with the 2 kb probe set (tat-rev) showing relatively little increase through the activation time course and the 9 kb full-length and 4 kb spliced probe sets showing a marked increase in level during activation (FIG. 9). Thus, the ratio of cell-based tat-rev to 4 kb/9 kb HIV RNA levels may be a useful measure of latent to active cell number.

For human sample testing (FIG. 10a-b) by HIV qLDR, CD4-enriched PBMC from HIV− and HIV+ participants were tested by the HIV qLDR probes SEQ ID NO: 9/SEQ ID NO: 10 for 2 kb tat-rev transcripts and SEQ ID NO: 5/SEQ ID NO: 6 for 9 kb and 4 kb transcripts. Lysates were tested from five individuals/class. Tests were performed in triplicate with 20 mL blood. As shown in FIG. 10a-b, HIV qLDR successfully detected cellular HIV RNA in HIV+ HAART (latent) samples, but not in HIV—samples, and further showed differential detection between latent and HIV+ non-HAART (active) samples, including viremic participants and elite controllers (FIG. 10a-b).

For human sample testing comparison with HIV RT-qPCR (FIG. 11), blood plasma was used for RT-qPCR and CD4+ T cells were used for qLDR. RT-qPCR was performed using primers and probe to the HIV gag-pol region, as described in Livak et al., 1995, for best comparison with HIV qLDR with probes SEQ ID NO: 1/SEQ ID NO: 2 to the HIV pol/protease region. HIV RNA was isolated from blood plasma samples prior to RT-qPCR. An RT-qPCR standard was prepared by in vitro transcription of a synthetic HIV T7 plasmid, and RNA copy number was determined using a standard curve generated with the RT-qPCR standard. Further, HIV qLDR results closely correlated with HIV RT-PCR viremia results for the same human peripheral blood samples (FIG. 11).

Example 6

Embodiments (Group A)

The following numbered items constitute certain nonlimiting embodiments described herein. Limitations in this section do not limit the claims or the other portions of the disclosure. These embodiments offer only some ways to operate according to the developments made herein. Other ways to operate according to the developments made herein are described in the specification and claims.

Item 1. A fluorogenic nucleic acid composition for quantitative detection of a target RNA sequence in a test sample, comprising:

(a) at least one pair of oligonucleotide or modified-backbone oligonucleotide probes comprising an upstream, first probe having a 5' end and a 3' end, and a downstream, second probe having a 5' end and a 3' end, forming a probe set of two probes;

(b) wherein the first probe and the second probe are complementary to an upstream and a downstream portion, respectively, of the target RNA sequence, and further wherein the upstream and downstream portions of the target RNA sequence proximately abut each other, such that an end of the first probe proximately abuts an end of the second probe to form probe-abutting ends on each of the two probes in some embodiments and not including background, when and only when both probes of the probe set hybridize to the target nucleic acid sequence; and (c) wherein one end of each of the first probe and the second probe is chemically attached to a nonfluorescent, reactive moiety, such that the nonfluorescent, reactive moieties on the probe-abutting ends of each of the two probes in the probe set are capable of reacting to form a covalent bond that produces a fluorescent compound whose fluorescence emissions are quantitatively detectable in some embodiments and not including background, when and only when both probes of the probe set hybridize to the target RNA sequence.

Item 2. A fluorogenic method for quantitative detection of a target ribonucleic acid (RNA) sequence in a test sample, comprising the steps of:

(a) preparing total or crude RNA from the test sample to form an RNA test solution;

(b) optionally preparing a dilution series from the RNA test solution to form a dilution series of RNA test solutions;

(c) adding to each RNA test solution a fluorescent-probe detection set for each target RNA sequence, in sufficient quantity to form an RNA detection solution comprising a uniform fluorescent-probe detection set final concentration in the range of 1 pM to 500 pM in each RNA detection solution;

(d) exposing each RNA detection solution to denaturing conditions;

(e) hybridizing the fluorescent-probe detection set for the target RNA sequence in each RNA detection solution at a temperature in the range of 40° C. to 60° C., under isothermal or thermocycling conditions;

(f) detecting with a detector the amount of fluorescence emitted by the fluorescent compound formed when the fluorescent-probe detection set hybridizes to the target RNA sequence in each RNA detection solution, wherein said detector comprises a source of light to excite the fluorescent compound in the excitation range of the fluorescent compound and a receiver in the emission range of the fluorescent compound to detect the fluorescence emitted by the fluorescent compound that has been excited in each RNA detection solution, wherein the amount of fluorescence emitted by the fluorescent compound in each RNA detection solution is detected;

(g) optionally normalizing the amount of fluorescence that is detected in each RNA detection solution to the amount of fluorescence that is detected in a parallel control sample that contains a non-target RNA sequence as a negative control; and (h) optionally normalizing the amount of fluorescence that is detected in each RNA detection solution to the amount of fluorescence that is detected in a parallel control sample that contains a modified target RNA sequence as a positive control; and (i) optionally calculating the amount of each target RNA sequence in the test sample from the normalized amount of fluorescence detected from each RNA detection solution.

Item 3. The fluorogenic nucleic acid composition of item 1, wherein the target RNA sequence is an HIV-1 sequence.

Item 4. The fluorogenic nucleic acid composition of item 1, wherein the at least one pair of oligonucleotide or modified-backbone oligonucleotide probes are selected from the group consisting of: the first probe comprising SEQ ID NO: 1 and the second probe comprising SEQ ID NO: 2; the first probe comprising SEQ ID NO: 3 and the second probe comprising SEQ ID NO: 4; the first probe comprising SEQ ID NO: 5 and the second probe comprising SEQ ID NO: 6; the first probe comprising SEQ ID NO: 7 and the second probe comprising SEQ ID NO: 8; the first probe comprising SEQ ID NO: 9 and the second probe comprising SEQ ID NO: 10; the first probe comprising SEQ ID NO: 11 and the second probe comprising SEQ ID NO: 12; the first probe comprising SEQ ID NO: 13 and the second probe comprising SEQ ID NO: 14; and, the first probe comprising SEQ ID NO: 15 and the second probe comprising SEQ ID NO: 16.

Item 5. The fluorogenic method of item 2, wherein the uniform fluorescent-probe detection set final concentration is in the range of 10 pM to 500 pM.

Item 6. The fluorogenic method of item 2, wherein the uniform fluorescent-probe detection set final concentration is in the range of 10 pM to 1 pM.

Item 7. The fluorogenic method of item 2, wherein the test sample is selected from the group consisting of: peripheral blood; lymph node; oral mucosa; gingival crevicular fluid (GCF); gut-associated lymphatic tissue (GALT), central nervous system (CNS) tissue, including brain tissue, cerebrospinal fluid (CSF), a mixed oral sample comprising oral mucosa, GCF, and saliva; and urine.

Item 8. A test kit for quantitative detection of cell-associated HIV-1 RNA in a test sample comprising (a) a fluorescent-probe detection set to detect 2 kb spliced HIV-1 RNA; (b) a fluorescent-probe detection set to detect 4 kb spliced and 9 kb full-length HIV-1 RNA; (c) a fluorescent-probe detection set to detect 9 kb full-length HIV-1 RNA; and (d) a concentrated reaction buffer comprising, after final dilution, a concentration of NaCl in the range of 100 mM to 150 mM and 10 mM potassium phosphate ($K_2HPO_4$) buffer at pH=7.4.

Item 9. A control kit for quantitative detection of cell-associated HIV-1 RNA in a test sample, comprising:

(1) a fluorescent-probe detection set to detect spliced CD4+ RNA;

(2) reference target RNA sequences comprising (a) 2 kb spliced HIV-1 RNA; (b) 4 kb spliced HIV-1 RNA; and (c) 9 kb full-length HIV-1 RNA;

(3) a control reference material comprising a control fluorescent-probe detection set and corresponding non-target RNA sequence; and (4) a concentrated reaction buffer comprising, after final dilution, a concentration of NaCl in the range of 100 mM to 150 mM and 10 mM potassium phosphate ($K_2HPO_4$) buffer at pH=7.4.

Example 7

Embodiments (Group B)

The following numbered embodiments constitute certain nonlimiting embodiments described herein. Limitations in this section do not limit the claims or the other portions of the disclosure. These embodiments offer only some ways to operate according to the developments made herein. Other ways to operate according to the developments made herein are described in the specification and claims.

Embodiment 1. A fluorogenic nucleic acid composition for quantitative detection of a target RNA sequence in a test sample comprising at least one pair of oligonucleotide probes with an upstream first probe and a downstream second probe complementary to and capable of specifically binding the target RNA in an upstream and downstream portion of the target RNA, respectively, wherein the at least one pair of oligonucleotide probes bind to a target RNA, wherein both probes are covalently bound to a nonfluorescent moiety, wherein the nonfluorescent moiety bound to the first probe chemically reacts with the nonfluorescent moiety on the second probe to form a fluorescent moiety covalently connecting the two probes when both probes of the probe set hybridize to the target RNA sequence; and wherein quantitative detection of target RNA may be performed by detecting the fluorescent signal generated.

Embodiment 2. The fluorogenic nucleic acid composition of embodiment 1, wherein the target RNA sequence is HIV-1, HIV-2, Ebola hemorrhagic fever, SARS, influenza (including but not limited to influenza A), hepatitis C, West Nile, polio, measles, CMV, Herpes, or Zika virus.

Embodiment 3. The fluorogenic nucleic acid composition of any one of embodiments 1-2, wherein the composition comprises more than one pair of oligonucleotide probes.

Embodiment 4. The fluorogenic nucleic acid composition of any one of embodiments 1-3, wherein the fluorogenic nucleic acid composition quantitatively detects 2 kb spliced HIV-1 RNA.

Embodiment 5.The fluorogenic nucleic acid composition of any one of embodiments 1-4, wherein the fluorogenic nucleic acid composition quantitatively detects 4 kb spliced and 9 kb full-length HIV-1 RNA.

Embodiment 6.The fluorogenic nucleic acid composition of any one of embodiments 1-5, wherein the fluorogenic nucleic acid composition quantitatively detects 9 kb full-length HIV-1 RNA.

Embodiment 7.The fluorogenic nucleic acid composition of any one of embodiments 1-6, wherein at least one pair of oligonucleotide probes comprises:
a. SEQ ID NO: 1 and 2;
b. SEQ ID NO: 3 and 4;
c. SEQ ID NO: 5 and 6;
d. SEQ ID NO: 7 and 8;
e. SEQ ID NO: 9 and 10;
f. SEQ ID NO: 11 and 12;
g. SEQ ID NO: 13 and 14;
h. SEQ ID NO: 15 and 16; and/or
i. any pair of oligonucleotide probes that vary by one or two nucleotides per probe from any of the pairs recited in (a)-(f).

Embodiment 8.T.he fluorogenic nucleic acid composition of embodiment 7, comprising more than one pair of oligonucleotide probes.

Embodiment 9..The fluorogenic nucleic acid composition of any one of embodiments 1-8, wherein the fluorogenic nucleic acid composition quantitatively detects spliced CD4+ RNA.

Embodiment 10..The fluorogenic nucleic acid composition of any one of embodiments 1-9, wherein the binding of the probes to the target RNA creates a gap between the probes.

Embodiment 11..The fluorogenic nucleic acid composition of embodiment 1-10, wherein, if the target RNA is linear, the upstream and downstream portions of the target RNA sequence have a gap of from 0-8 nucleotides corresponding to the gap between the probes.

Embodiment 12.The fluorogenic nucleic acid composition of any one of embodiments 1-11, wherein the nonfluorescent moiety is bound to the downstream end of the upstream first probe and wherein the nonfluorescent moiety is bound to the upstream end of the downstream second probe.

Embodiment 13.The fluorogenic nucleic acid composition of any one of embodiments 1-12, wherein at least one of the oligonucleotide probes comprise modified-backbone nucleotides.

Embodiment 14.The fluorogenic nucleic acid composition of embodiment 13, wherein the at least one modified-backbone oligonucleotide probe comprises protein nucleic acid (PNA) probes, bridged nucleic acids (BNA), locked nucleic acids (LNA), and guanidine-modified PNA (GPNA).

Embodiment 15.The fluorogenic nucleic acid composition of any one of embodiments 13-14, wherein both probes in a pair comprise modified-backbone nucleotides.

Embodiment 16. The fluorogenic nucleic acid composition of embodiment 15, wherein the two probes in a pair comprise different types of modified-backbone nucleotides.

Embodiment 17. The fluorogenic nucleic acid composition of any one of embodiments 13-14, wherein one probe in a pair comprises modified-backbone nucleotides.

Embodiment 18. The fluorogenic nucleic acid composition of any one of embodiments 1-17, wherein the oligonucleotide probes are from 5 to 30 oligonucleotides long or from 18 to 21 oligonucleotides long.

Embodiment 19. The fluorogenic nucleic acid composition of any one of embodiments 1-18, wherein the fluorescent moiety formed comprises any one of the fluorescent dyes provided in Table 3.

Embodiment 20. A fluorogenic method for quantitative detection of a target ribonucleic acid (RNA) sequence in a sample comprising:
a. adding to the sample a fluorogenic nucleic acid composition comprising at least one pair of oligonucleotide probes with an upstream first probe and a downstream second probe complementary to and capable of specifically binding the target RNA in an upstream and downstream portion of the target RNA, respectively, wherein
  i. the at least one pair of oligonucleotide probes bind to a target RNA,
  ii. both probes are covalently bound to a nonfluorescent moiety, and
  iii. the nonfluorescent moiety bound to the first probe chemically reacts with the nonfluorescent moiety on the second probe to form a fluorescent moiety covalently connecting the two probes when both probes of the probe set hybridize to the target nucleic acid sequence;
b. optionally exposing the sample to denaturing conditions;
c. hybridizing the probes in the fluorogenic nucleic acid composition; and
d. detecting the amount of fluorescence emitted by the fluorescent moiety covalently connecting the two probes when both probes of the probe set hybridize to the target nucleic acid sequence.

Embodiment 21. The method of embodiment 20, wherein the fluorogenic nucleic composition added to the sample is the fluorogenic nucleic acid composition of any one of embodiments 2-19.

Embodiment 22. The method of any one of embodiments 20-21, wherein the sample is exposed to denaturing conditions.

Embodiment 23. The method of embodiment 22, wherein the denaturing conditions comprise temperature of from 50-100° C. and/or chemical denaturants.

Embodiment 24. The method of any one of embodiments 20-23, wherein the hybridizing of the probes occurs at a temperature of from 35° C. to 70° C.

Embodiment 25. The method of any one of embodiments 20-24, wherein the hybridizing of the probes occurs at isothermal conditions.

Embodiment 26. The method of any one of embodiments 20-25, wherein the hybridizing of the probes occurs at thermocycling conditions.

Embodiment 27. The method of any one of embodiments 20-26, wherein the method further comprises normalizing the amount of fluorescence that is detected to the amount of fluorescence that is detected in a negative control sample that contains a non-target RNA sequence.

Embodiment 28. The method of any one of embodiments 20-27, wherein the method further comprises normalizing the amount of fluorescence that is detected to the amount of fluorescence that is detected in a positive control sample that contains a target RNA sequence of known concentration.

Embodiment 29. The method of any one of embodiments 27-28, wherein the method further comprises calculating the amount of each target RNA sequence in the test sample from the normalized amount of fluorescence detected.

Embodiment 30. The fluorogenic method of any one of embodiments 20-29, wherein the first and second probes of the probe set are at a concentration of from 1 pM to 1 µM when mixed with the sample and in the reaction conditions.

Embodiment 31. The fluorogenic method of any one of embodiments 20-30, wherein the test sample comprises mixed RNA species from cells.

Embodiment 32. The fluorogenic method of any one of embodiments 20-31, wherein the test sample is chosen from peripheral blood; lymph node; oral mucosa; gingival crevicular fluid (GCF); gut-associated lymphatic tissue (GALT), central nervous system (CNS) tissue, including brain tissue, cerebrospinal fluid (CSF), a mixed oral sample comprising oral mucosa, GCF, and saliva, and urine.

Embodiment 33. The fluorogenic method of any one of embodiments 20-32, wherein the method can detect a target sequence in single-stranded RNA.

Embodiment 34. The fluorogenic method of any one of embodiments 20-33, wherein the method can detect a target sequence in an RNA hairpin or an RNA pseudoknot or other RNA secondary, tertiary, or quaternary structure.

Embodiment 35. The fluorogenic method of any one of embodiments 20-34, wherein the method can detect a target sequence so as to identify the presence or absence of a mutation in RNA or an RNA splicing product.

Embodiment 36. The fluorogenic method of any one of embodiments 20-35, wherein the method can detect a target sequence with less than or equal to 5% variation in the target sequence.

Embodiment 37. The fluorogenic method of any one of embodiments 20-36, further comprising administering an anti-HIV medication to a patient and performing the fluorogenic method on samples obtained from the patient before and after the medication was administered.

Embodiment 38. The fluorogenic method of embodiment 37, wherein the anti-HIV medication is undergoing clinical trials.

Embodiment 39. The fluorogenic method of embodiment 20-38, wherein the method is conducted to determine if the patient's HIV strain(s) are susceptible to the anti-HIV medication.

Embodiment 40. The fluorogenic method of any one of embodiments 37-39, wherein sample is obtained from the patient and an anti-HIV medication is administered to the patient if the patient is found to have a latent HIV reservoir.

Embodiment 41. A test kit for quantitative detection of cell-associated HIV-1 RNA in a test sample comprising the fluorogenic nucleic acid composition of any one of embodiments 1 to 19 and at least one buffer.

Embodiment 42. The test kit of embodiment 41, wherein the at least one buffer is a reaction buffer.

Embodiment 43. The test kit of embodiment 42, wherein the reaction buffer comprises sodium chloride (NaCl) and potassium phosphate ($K_2HPO_4$).

Embodiment 44. The test kit of embodiment 43, wherein the reaction buffer at final concentration comprises from 100 mM to 150 mM NaCl and from 5 mM to 15 mM $K_2HPO_4$.

Embodiment 45. The test kit of any one of embodiment 42-44, wherein the reaction buffer at final concentration comprises 10 mM $K_2HPO_4$ and has a pH of 7.4.

Embodiment 46. The test kit of any one of embodiments 41-45, wherein the test kit comprises at least one pair of oligonucleotide probes to quantitatively detect spliced CD4+ RNA.

Embodiment 47 The test kit of any one of embodiments 41-46, wherein the test kit comprises a positive control.

Embodiment 48. The test kit of any one of embodiments 41-47, wherein the test kit comprises a negative control.

Embodiment 49. The test kit of embodiment 48, wherein the negative control comprises a non-target RNA sequence.

All references cited throughout the entirety of the foregoing specification are hereby expressly incorporated by reference for their entire disclosure.

To the extent embodiments have been described with reference to what is considered to be specific embodiments, it is to be understood that the claims are not so limited. Other embodiments will be apparent to those skilled in the art from consideration of the specification and practice as disclosed herein. The application is accordingly intended to cover various modifications and equivalents included within the spirit and scope of the recited claims.

REFERENCES

Koripelly G, Meguellati K, Ladame S. Dual sensing of hairpin and quadruplex DNA structures using multicolored peptide nucleic acid fluorescent probes. Bioconjug. Chem. 2010. 21:2103-9.

Livak K J, Flood S J, Marmaro J, Giusti W, Deetz K. Oligonucleotides with fluorescent dyes at opposite ends provide a quenched probe system useful for detecting PCR product and nucleic acid hybridization. PCR Methods Appl. 1995. 4:357-362.

Meguellati K, Koripelly G, Ladame S. DNA-templated synthesis of trimethine cyanine dyes: a versatile fluorogenic reaction for sensing G-quadruplex formation. Angew Chem. Int. Ed. Engl. 2010. 49:2738-2742.

Meguellati K, Koripelly G, Ladame S. Single nucleotide polymorphism detection using a biocompatible, fluorogenic and DNA-templated reaction of cyanine dye formation. J. Analyt. Molecul. Tech. 2013. 1(1):5.

The foregoing written specification is considered to be sufficient to enable one skilled in the art to practice the embodiments. The foregoing description and Examples detail certain embodiments and describes the best mode contemplated by the inventors. It will be appreciated, however, that no matter how detailed the foregoing may appear in text, the embodiment may be practiced in many ways and should be construed in accordance with the appended claims and any equivalents thereof.

As used herein, the term about refers to a numeric value, including, for example, whole numbers, fractions, and percentages, whether or not explicitly indicated. The term about generally refers to a range of numerical values (e.g., +/−5-10% of the recited range) that one of ordinary skill in the art would consider equivalent to the recited value (e.g., having the same function or result). When terms such as at least and about precede a list of numerical values or ranges, the terms modify all of the values or ranges provided in the list. In some instances, the term about may include numerical values that are rounded.

We claim:

1. A fluorogenic method for quantitative detection of a target ribonucleic acid (RNA) sequence in a test sample comprising:
   a. adding to the sample a fluorogenic nucleic acid composition comprising an excess of at least one pair of oligonucleotide probes with an upstream first probe and a downstream second probe complementary to and capable of specifically binding the target RNA in an upstream and downstream portion of the target RNA, respectively, wherein both probes are covalently bound to a nonfluorescent moiety;
   b. optionally exposing the sample to denaturing conditions;
   c. hybridizing the probes in the fluorogenic nucleic acid composition wherein:
      i. the at least one pair of oligonucleotide probes bind to a target RNA, and
      ii. the nonfluorescent moiety bound to the first probe chemically reacts with the nonfluorescent moiety on the second probe to form a fluorescent moiety covalently connecting the two probes when both probes of the probe set hybridize to the target RNA sequence;

d. allowing the probes and covalently bound fluorescent moiety bridging the probes to fall off the target RNA under temperature conditions in which the covalently connected probe pair is capable of falling off the target RNA and wherein the fluorescent moiety covalently connecting the two probes remains intact;

e. repeating step c;

f. optionally repeating step d and c one or more times; and g. detecting the amount of fluorescence emitted by the fluorescent moiety in the sample covalently connecting the two probes.

2. The method of claim 1, wherein the target RNA sequence is HIV-1, HIV-2, Ebola hemorrhagic fever, SARS, influenza, hepatitis C, West Nile, polio, measles, CMV, Herpes, or Zika virus.

3. The method of claim 1, wherein in step b the sample is exposed to denaturing conditions.

4. The method of claim 1, wherein the method further comprises normalizing the amount of fluorescence that is detected in the test sample to the amount of fluorescence that is detected in a negative control sample that contains a non-target RNA sequence and calculating the amount of each target RNA sequence in the test sample from the normalized amount of fluorescence detected.

5. The method of claim 1, wherein the method further comprises normalizing the amount of fluorescence that is detected in the test sample to the amount of fluorescence that is detected in a positive control sample that contains a target RNA sequence of known concentration and calculating the amount of each target RNA sequence in the test sample from the normalized amount of fluorescence detected.

6. The fluorogenic method of claim 1, further comprising administering an anti-HIV medication to a patient and performing the fluorogenic method on samples obtained from the patient before and after the medication was administered.

7. The fluorogenic method of claim 1, wherein the sample is obtained from a patient, further comprising measuring a level of D4-A7 spliced site in the sample, wherein D4-A7 splicing indicates a latent HIV reservoir, and administering an anti-HIV medication to the patient if the patient is found to have a latent HIV reservoir.

8. The method of claim 1, wherein step d occurs under denaturing conditions.

9. The method of claim 8, wherein step d occurs at a temperature of from 90° C. to 100° C.

10. The method of claim 1, wherein step d occurs under isothermal conditions.

11. The method of claim 10, wherein step d occurs at a temperature of from 20° C. to 70° C.

12. The method of claim 1, wherein steps c-d occur under thermocycling conditions.

13. The method of claim 12, wherein step d occurs at a temperature of from 90° C. to 100° C. and step c occurs at a temperature of from 20° C. to 70° C.

* * * * *